US008152991B2

(12) United States Patent
Briman et al.

(10) Patent No.: US 8,152,991 B2
(45) Date of Patent: Apr. 10, 2012

(54) AMMONIA NANOSENSORS, AND ENVIRONMENTAL CONTROL SYSTEM

(75) Inventors: Mikhail Briman, Emeryville, CA (US); Craig Bryant, Alameda, CA (US); Ying-Lan Chang, Cupertino, CA (US); Jean-Christophe P. Gabriel, Pinole, CA (US); Shirpal C. Gandhi, Los Angeles, CA (US); Bradley N Johnson, Berkeley, CA (US); Willem-Jan Ouborg, Moraga, CA (US); John Loren Passmore, Berkeley, CA (US); Kastooriranganathan Ramakrishnan, San Rafael, CA (US); Sergei Skarupo, Berkeley, CA (US); Alexander Star, Pittsburgh, PA (US); Christian Valcke, Orinda, CA (US)

(73) Assignee: Nanomix, Inc., Emeryville, CA (US)

( * ) Notice: Subject to any disclaimer, the term of this patent is extended or adjusted under 35 U.S.C. 154(b) by 877 days.

(21) Appl. No.: 11/636,360

(22) Filed: Dec. 8, 2006

(65) Prior Publication Data
US 2008/0093226 A1 Apr. 24, 2008

Related U.S. Application Data

(63) Continuation-in-part of application No. 11/588,845, filed on Oct. 26, 2006, now abandoned.

(60) Provisional application No. 60/748,834, filed on Dec. 9, 2005, provisional application No. 60/730,905, filed on Oct. 27, 2005, provisional application No. 60/850,217, filed on Oct. 6, 2006, provisional application No. 60/773,138, filed on Feb. 13, 2006.

(51) Int. Cl.
*G01N 27/26* (2006.01)
(52) U.S. Cl. ........ 205/775; 205/778; 205/781; 205/782; 205/782.5; 205/783; 205/785.5; 205/786; 205/787; 205/792; 205/794.5
(58) Field of Classification Search ............ 204/403.01, 204/403.06, 403.13, 403.15, 406, 412, 424, 204/431, 433; 422/68.1, 81, 82.01, 82.02, 422/82.03, 83, 88, 90, 98; 205/775, 778, 205/781, 782, 782.5, 783, 785.5, 786, 787, 205/792, 794.5
See application file for complete search history.

(56) References Cited

U.S. PATENT DOCUMENTS

| | | | |
|---|---|---|---|
| 3,860,430 A | 1/1975 | Walker et al. | |
| 4,022,059 A * | 5/1977 | Schontzler et al. | 73/198 |
| 4,795,968 A | 1/1989 | Madou et al. | |
| 4,851,195 A | 7/1989 | Matthews et al. | |
| 4,909,919 A * | 3/1990 | Morris et al. | 204/603 |
| 5,246,859 A | 9/1993 | Nelson et al. | |
| 5,258,415 A | 11/1993 | Hahn et al. | |
| 5,382,417 A | 1/1995 | Haase | |
| 5,448,905 A * | 9/1995 | Stetter et al. | 73/31.05 |
| 5,618,496 A | 4/1997 | Hasumi et al. | |
| 5,759,773 A | 6/1998 | Tyagi et al. | |
| 5,958,340 A | 9/1999 | Meyer et al. | |
| 6,004,494 A | 12/1999 | Debe | |
| 6,010,459 A | 1/2000 | Silkoff et al. | |
| 6,031,454 A | 2/2000 | Lovejoy et al. | |
| 6,044,843 A | 4/2000 | O'Neil et al. | |
| 6,090,545 A | 7/2000 | Wohlstadter et al. | |
| 6,111,280 A | 8/2000 | Gardner et al. | |
| 6,217,828 B1 | 4/2001 | Bretscher et al. | |
| 6,286,226 B1 | 9/2001 | Jin | |
| 6,465,132 B1 | 10/2002 | Jin | |
| 6,489,394 B1 | 12/2002 | Andros | |
| 6,528,020 B1 | 3/2003 | Dai et al. | |
| 6,577,242 B2 | 6/2003 | Jen et al. | |
| 6,797,325 B2 | 9/2004 | Wang et al. | |
| 6,894,359 B2 | 5/2005 | Bradley et al. | |
| 7,109,859 B2 | 9/2006 | Peeters | |
| 7,271,720 B2 | 9/2007 | Tabe | |
| 7,312,095 B1 | 12/2007 | Gabriel et al. | |
| 7,522,040 B2 | 4/2009 | Passmore et al. | |
| 7,547,931 B2 | 6/2009 | Star et al. | |
| 2002/0012937 A1 | 1/2002 | Tender et al. | |
| 2002/0017300 A1 | 2/2002 | Hickle et al. | |
| 2002/0092779 A1 | 7/2002 | Essalik et al. | |
| 2002/0117659 A1 | 8/2002 | Lieber et al. | |
| 2002/0127623 A1 * | 9/2002 | Minshull et al. | 435/7.92 |
| 2002/0127733 A1 | 9/2002 | Kovacs | |
| 2003/0031620 A1 | 2/2003 | Harutyunyan et al. | |
| 2003/0036065 A1 | 2/2003 | Gellibolian | |
| 2003/0041438 A1 | 3/2003 | Wei et al. | |

(Continued)

FOREIGN PATENT DOCUMENTS

JP 2003-517604 5/2003

(Continued)

OTHER PUBLICATIONS

US Office Action mailed Jul. 14, 2008, U.S. Appl. No. 11/019,792.
Suri et al. (2002) Gas and Humidity Sensors Based on Iron Oxide-Polyprrole Nanocomposites, Sensors and Actuators, B 81, pp. 277-282.
Notice of Allowance mailed Feb. 11, 2009, for U.S. Appl. No. 11/019,792.
US application titled, "Nanoelectronic Capnometer Adapter including a Nanoelectronic Sensor Selectively Sensitive to at Least one Gaseous Consitutent of Exhaled Breath," U.S. Appl. No. 12/485,793, filed Jun. 16, 2009.

(Continued)

*Primary Examiner* — Bruce Bell
(74) *Attorney, Agent, or Firm* — Weaver Austin Villeneuve & Sampson LLP

(57) ABSTRACT

Embodiments of nanoelectronic sensors are described, including sensors for detecting analytes such ammonia. An environmental control system employing nanoelectronic sensors is described. A personnel safety system configured as a disposable badge employing nanoelectronic sensors is described. A method of dynamic sampling and exposure of a sensor providing a number of operational advantages is described.

22 Claims, 15 Drawing Sheets

U.S. PATENT DOCUMENTS

| | | | |
|---|---|---|---|
| 2003/0068432 A1 | 4/2003 | Dai et al. | |
| 2003/0073919 A1 | 4/2003 | Hampton et al. | |
| 2003/0134267 A1 | 7/2003 | Kang et al. | |
| 2003/0139003 A1 | 7/2003 | Gole et al. | |
| 2003/0175161 A1 | 9/2003 | Gabriel et al. | |
| 2003/0211637 A1 | 11/2003 | Schoeniger et al. | |
| 2004/0011291 A1 | 1/2004 | Delaunay et al. | |
| 2004/0018587 A1 | 1/2004 | Makowski et al. | |
| 2004/0023428 A1 | 2/2004 | Gole et al. | |
| 2004/0033525 A1 | 2/2004 | Monforte et al. | |
| 2004/0043527 A1 | 3/2004 | Bradley et al. | |
| 2004/0067530 A1 | 4/2004 | Gruner et al. | |
| 2004/0091285 A1 | 5/2004 | Lewis | |
| 2004/0120183 A1 | 6/2004 | Appenzeller et al. | |
| 2004/0136866 A1 | 7/2004 | Pontis et al. | |
| 2004/0158410 A1 | 8/2004 | Ono et al. | |
| 2004/0192072 A1 | 9/2004 | Snow et al. | |
| 2004/0204915 A1* | 10/2004 | Steinthal et al. | 702/188 |
| 2004/0214176 A1 | 10/2004 | Osborne et al. | |
| 2004/0219090 A1 | 11/2004 | Dziedzic et al. | |
| 2005/0003355 A1 | 1/2005 | Lu et al. | |
| 2005/0065741 A1 | 3/2005 | Segal et al. | |
| 2005/0103097 A1 | 5/2005 | Fultum et al. | |
| 2005/0129573 A1 | 6/2005 | Gabriel et al. | |
| 2005/0211572 A1* | 9/2005 | Buck et al. | 205/778 |
| 2005/0245836 A1 | 11/2005 | Star et al. | |
| 2006/0009707 A1 | 1/2006 | Daniels et al. | |
| 2006/0009797 A1 | 1/2006 | Armstrong | |
| 2006/0014172 A1 | 1/2006 | Muller et al. | |
| 2006/0021881 A1 | 2/2006 | Soundarrajan et al. | |
| 2006/0035215 A9 | 2/2006 | Sorge et al. | |
| 2006/0040294 A1 | 2/2006 | Prudent et al. | |
| 2006/0055392 A1 | 3/2006 | Passmore et al. | |
| 2006/0102494 A1* | 5/2006 | Chueh et al. | 205/785.5 |
| 2006/0232278 A1* | 10/2006 | Diamond et al. | 324/444 |
| 2006/0249402 A1 | 11/2006 | Snow et al. | |
| 2007/0048180 A1 | 3/2007 | Gabriel et al. | |
| 2007/0048181 A1 | 3/2007 | Chang et al. | |
| 2007/0114138 A1 | 5/2007 | Krasteva et al. | |
| 2007/0178477 A1 | 8/2007 | Joiner et al. | |
| 2007/0259359 A1 | 11/2007 | Briman et al. | |
| 2007/0281156 A1 | 12/2007 | Lieber et al. | |
| 2008/0021339 A1 | 1/2008 | Gabriel et al. | |
| 2010/0085067 A1 | 4/2010 | Gabriel et al. | |
| 2010/0137731 A1 | 6/2010 | Star et al. | |

FOREIGN PATENT DOCUMENTS

| | | |
|---|---|---|
| WO | 01/44796 | 6/2001 |
| WO | WO 02/48701 | 6/2002 |
| WO | WO 2004/065404 | 8/2004 |
| WO | WO 2005/026694 | 3/2005 |
| WO | WO 2005/033707 | 4/2005 |
| WO | WO 2005/062031 | 7/2005 |
| WO | 2007/114931 | 10/2007 |
| WO | WO 2008/039165 | 4/2008 |

OTHER PUBLICATIONS

US Office Action mailed Jul. 26, 2010, U.S. Appl. No. 12/485,793.
US application titled, "Nanoelectronic Breath Analyzer and Asthma Monitor," U.S. Appl. No. 11/437,275, filed May 18, 2006.
US Office Action mailed May 12, 2008, U.S. Appl. No. 11/437,275.
US Final Office Action mailed Feb. 3, 2009, U.S. Appl. No. 11/437,275.
International Written Opinion mailed Aug. 7, 2008 for Application No. PCT/US2007/010836.
US application titled, "Carbon Dioxide Nanosensor, and Respiratory CO2 Monitors," U.S. Appl. No. 11/488,456, filed Jul. 18, 2006.
US Office Action mailed Apr. 16, 2008, U.S. Appl. No. 11/488,456.
US Final Office Action mailed Jan. 14, 2009, U.S. Appl. No. 11/488,456.
International Search Report and Written Opinion mailed Oct. 27, 2008 for Application No. PCT/US2007/008422.
Star, et al., "Label-Free Detection of DNA Hybridization Using Carbon Nanotube Network field-Effect Transistors," Peox. Nat'l. Acad. Sci. USA, vol. 103, No. 4, Jan. 24, 2006, p. 921-926.
International Search Report and Written Opinion mailed Nov. 10, 2009 for Application No. 07754869.1.
Lee, et al. "Enzymatically Amplified Surface Plasmon Resonance Imaging detection of DNA by Exonuclease III Digestion of DNA Microarrays," Chemical Society US, Aug. 15, 2005, vol. 77, No. 16, pp. 5096-5100.
Goodrich, Terry, et al, Direct Detection of Genomic DNA by Enzymatically Amplified SPR Imaging Measurements of RNA Microarrays, Journal of the American Chemical Society, vol. 126, No. 13, Apr. 7, 2004, p. 4086-4087.
Baeumner. A.J., et al., "A Universal Nucleic Acid Sequence Biosensor With Nanomolar Detection Limits," Analytical Chemistry 20040215, American Chemical Society, vol. 76, No. 4, Jan. 1, 2004, pates 888-894.
Duck, et al., "Probe Amplifier System Based on Chimeric Cycling Obigonucleotides," Biotechniques, Natick, MA, vol. 9, No. 2, Jan. 1, 1990, XP000406092, Abstract; Figure 1.
US application titled, "Anesthesia Monitor, Capacitance Nanosensors and Dynamic Sensor Sampling Method," U.S. Appl. No. 11/588,845, filed Oct. 26, 2006.
US Office Action mailed Mar. 17, 2009, for U.S. Appl. No. 11/588,845.
US application titled, "Anesthesia Monitor, Capacitance Nanosensors and Dynamic Sensor Sampling Method," U.S. Appl. No. 12/560,316, filed Sep. 15, 2009.
US Office Action mailed Apr. 1, 2008, for U.S. Appl. No. 11/111,121.
US Notice of Allowance Mailed Oct. 8, 2008, for U.S. Appl. No. 11/111,121.
US Office Action Final dated Feb. 10, 2011 issued in U.S. Appl. No. 12/485,793.
US Office Action Final dated Feb. 3, 2009 issued in U.S. Appl. No. 11/437,275.
US Office Action dated Oct. 7, 2010 issued in U.S. Appl. No. 12/560,316.
US Office Action Final dated Jun. 28, 2011 issued in U.S. Appl. No. 12/560,316.
US Office Action dated Jun. 1, 2005 issued in U.S. Appl. No. 10/940,324.
US Office Action dated Mar. 3, 2006 issued in U.S. Appl. No. 10/940,324.
US Office Action dated Sep. 7, 2006 issued in U.S. Appl. No. 10/940,324.
US Office Action Final dated Feb. 21, 2007 issued in U.S. Appl. No. 10/940,324.
US Office Action dated Aug. 27, 2007 issued in U.S. Appl. No. 10/940,324.
US Office Action Final dated May 27, 2008 issued in U.S. Appl. No. 10/940,324.
US Office Action dated Aug. 12, 2008 issued in U.S. Appl. No. 10/940,324.
US Office Action dated Apr. 16, 2009 issued in U.S. Appl. No. 10/940,324.
PCT International Search Report Jun. 11, 2008 issued in PCT/US06/28079 (WO 2008/039165).
PCT International Preliminary Report on Patentability and Written Opinion dated Jul. 1, 2008 issued in PCT/US06/28079 (WO 2008/039165).
PCT International Preliminary Report on Patentability and Written Opinion dated Nov. 18, 2008 issued in PCT/US2007/10836 (WO 2007/136523).
EP Extended European Search Report and Supplementary European Search Report dated Aug. 30, 2011 issued in EP 07 756 204.9.
PCT International Search Report dated Sep. 22, 2005 issued in PCT/US2004/030136 (WO 2005/026694).
PCT International Written Opinion dated Sep. 22, 2005 issued in PCT/U52004/030136 (WO 2005/026694).
PCT International Preliminary Report on Patentability and Written Opinion dated Jul. 31, 2006 issued in PCT/US2004/030136 (WO 2005/026694).
European Search Report dated Mar. 30, 2007 issued in EP 04 788 761.

European Examination Report dated Feb. 10, 2010 issued in EP 04 788 761.7.
Japanese Office Action dated Jul. 13, 2010 issued in JP 2006-526418.
Ong et al., (Nov. 2, 2001) "A Carbon Nanotube-based Sensor for $CO_2$ Monitoring", *Sensors*, MDPT, Basel, SU, 1(6):193-205.
Qi et al., (2003) "Toward Large Arrays of Multiplex Functionalized Carbon Nanoturbe Sensors for Highly Sensitive and Selective Molecular Detection", *NANO Letters*, 3(3):347-351.

Stetter et al., (Feb. 23, 2003) "Nano-Electronic Sensors; Practical Device Designs for Sensors", *Nanotechnology Conference and Trade Show, Nanotech, Joint Meeting, International Conference on Modeling and Simulation of Microsystems, MSM, International Conference on Computational Nanoscience and Technology*, 3(23):313-316.

* cited by examiner

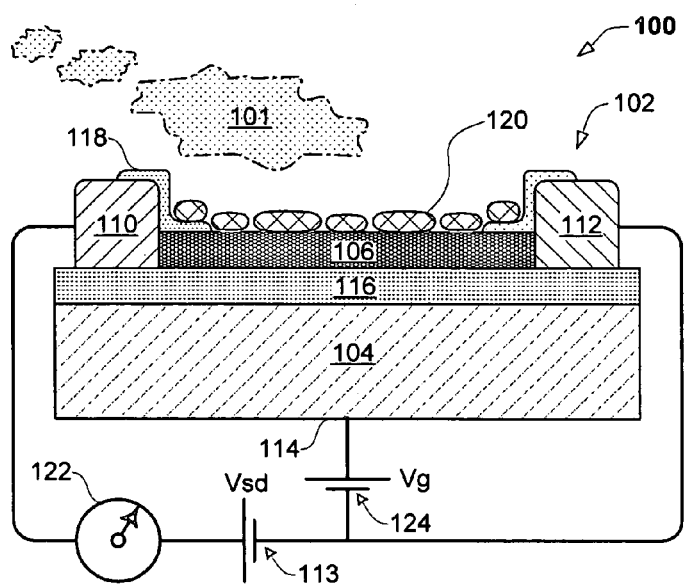
FIG. 1
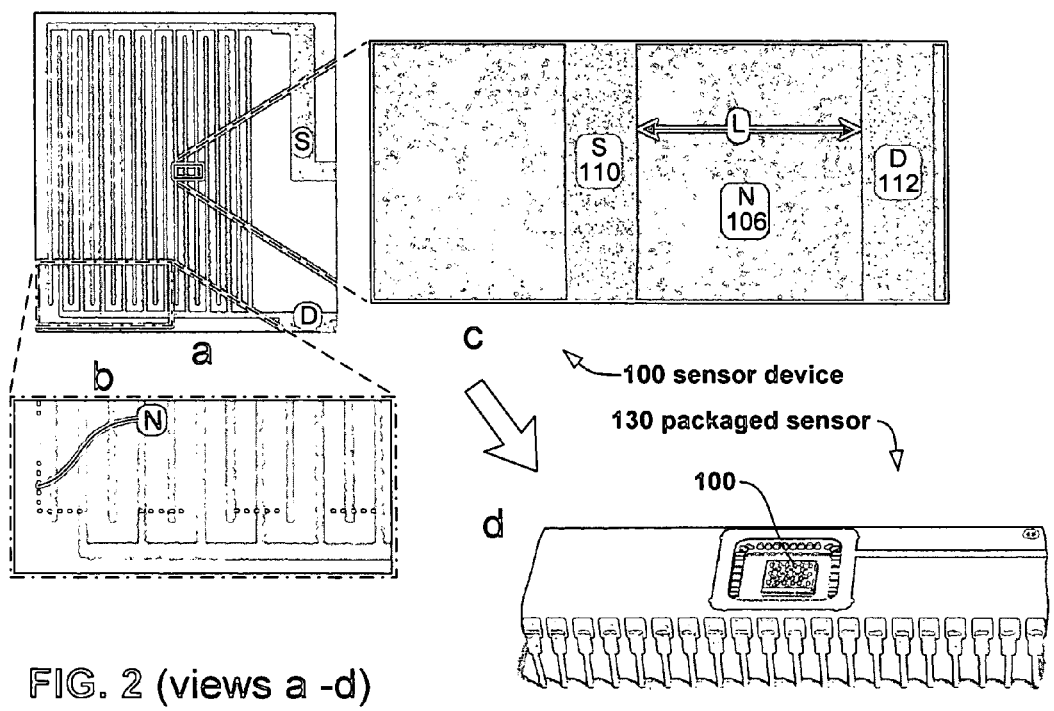
FIG. 2 (views a-d)

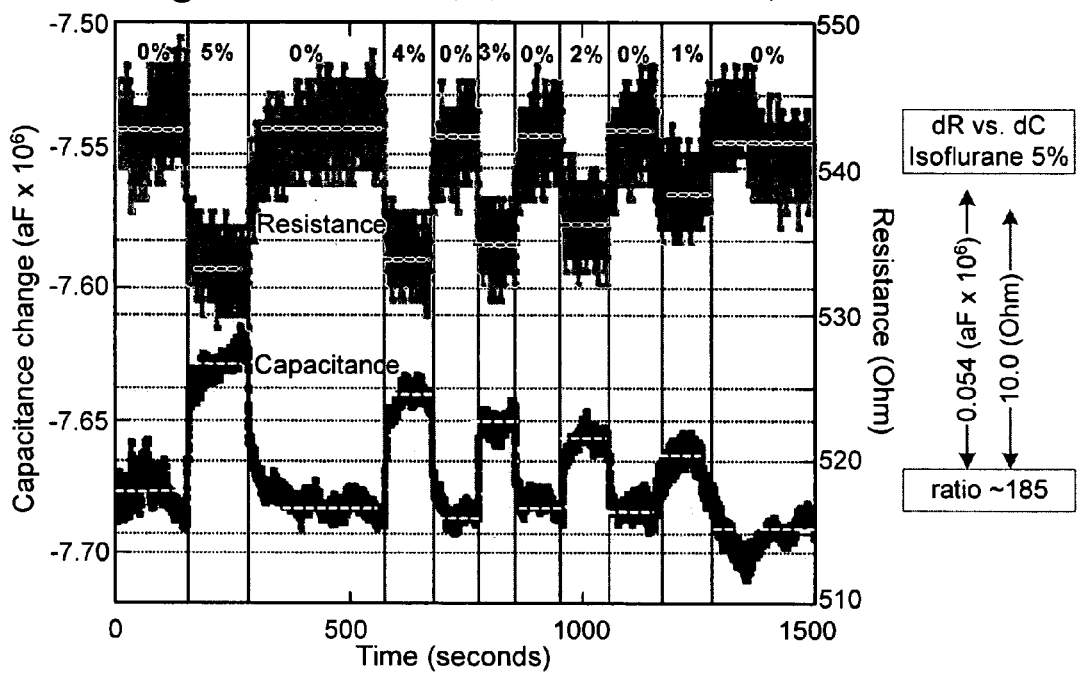
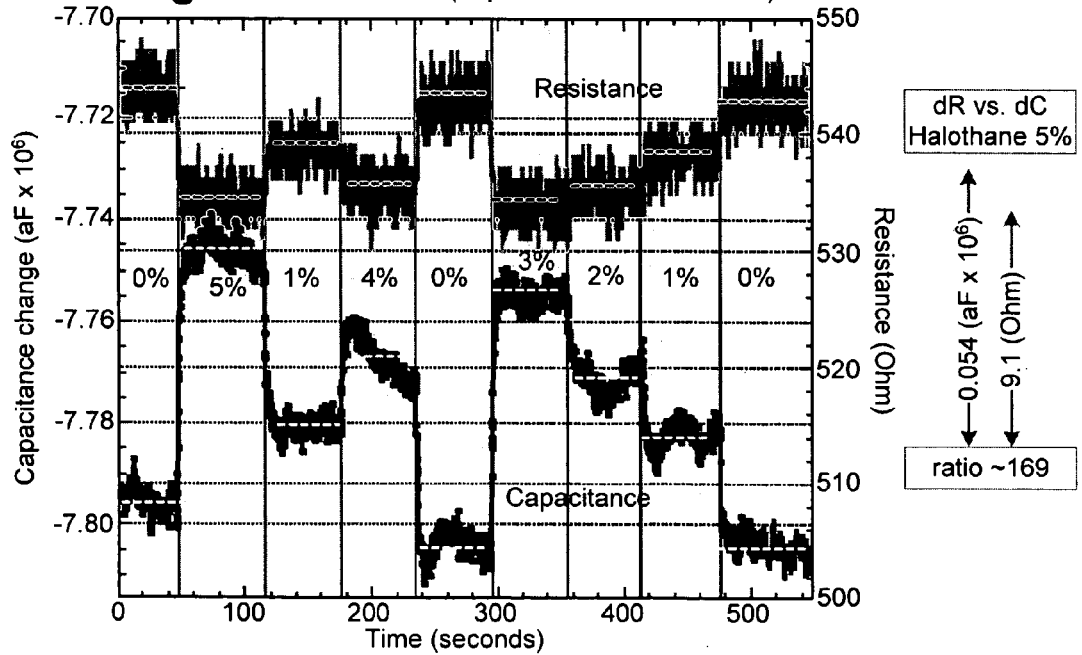

AMMONIA NANOSENSORS, AND ENVIRONMENTAL CONTROL SYSTEM

CROSS-REFERENCE TO RELATED APPLICATIONS

This application claims priority pursuant to 35 USC §119 (e) to US Provisional Application Ser. No. 60/748,834 filed Dec. 9, 2005. This application is also a continuation-in-part of and claims priority to U.S. Patent Application No. 11/588,845 (now abandoned), filed Oct. 26, 2006, which in turn claims priority pursuant to 35 USC §119(e) to the following U.S. provisional applications: U.S. Provisional Application No. 60/730,905, filed Oct. 27, 2005; U.S. Provisional Application No. 60/850,217, filed Oct. 6, 2006; and U.S. Provisional Application No. 60/773,138, filed Feb. 13, 2006. These applications are incorporated herein by this reference.

The following U.S. provisional and non-provisional patent applications are incorporated by reference:
Ser. No. 11/488,456 (now abandoned) filed Jul. 18, 2006 (published 2007-0048181) entitled "Improved Carbon Dioxide Nanosensor, And Respiratory CO2 Monitors",
Ser. No. 11/437,275 (now abandoned) filed May 18, 2006 (published 2007-0048180) entitled "Nanoelectronic Breath Analyzer and Asthma Monitor",
Ser. No. 11/390,493 (now U.S. Pat. No. 7,714,398) filed Mar. 27, 2006 (published 2010-0056892) entitled "Nanoelectronic Measurement System For Physiologic Gases, And Improved Nanosensor For Carbon Dioxide",
Ser. No. 11/111,121 (U.S. Pat. No. 7,522,040) filed Apr. 20, 2005 (published 2006-0055392-A1) entitled "Remotely communicating, battery powered nanostructure sensor devices",
Ser. No. 11/019,792 (now U.S. Pat. No. 7,547,931) filed Dec. 18, 2004 (published 2005-0245836) entitled "Nanoelectronic capnometer adapter",
Ser. No. 10/940,324 (now abandoned) filed Sep. 13, 2004 (published 2005-0129573) entitled "Carbon Dioxide Nanoelectronic Sensor",
Ser. No. 10/656,898 (now abandoned) filed Sep. 5, 2003 (published 20050279987) entitled "Polymer Recognition Layers For Nanostructure Sensor Devices",
No. 60/700,944 filed Jul. 20, 2005,
No. 60/683,460 filed May 19, 2005,
No. 60/665,153 filed Mar. 25, 2005,
No. 60/564,248, filed Apr. 20, 2004,
No. 60/531,079 filed Dec. 18, 2003,
No. 60/502,485 filed Sep. 12, 2003, and No. 60/408,547 filed September 5, 2002.

This application is related in subject matter to U.S. patent application Ser. No. 11/090,550 (now abandoned) filed Mar. 25, 2005 (published 2005-0169798) entitled "Sensitivity Control For Nanotube Sensors", which is a divisional of Ser. No. 10/280,265 (now abandoned) filed Oct. 26, 2002 (U.S. Pat. No. 6,894,359), which claims priority to U.S. Application No. 60/408,412 filed Sep. 4, 2002; each of which applications are incorporated by reference.

This application is related in subject matter to U.S. patent application Ser. No. 10/846,072 (U.S. Pat. No. 7,956,525) filed May 14, 2004 (published 2005-0184641) entitled "Flexible Nanotube Transistors", which claims priority to U.S. No. 60/471,243 filed May 16, 2003; each of which applications are incorporated by reference.

This application is related in subject matter to U.S. patent application Ser. No. 10/177,929 (now abandoned) filed Jun. 21, 2002 entitled "Dispersed Growth Of Nanotubes On A Substrate" (equivalent published as W004-040,671); each of which applications are incorporated by reference.

This application is related in subject matter to U.S. patent application Ser. No. 11/139,184 (U.S. Pat. No. 7,575,933) filed May 27, 2005 (published 2006-0078468) entitled "Modification Of Selectivity For Sensing For25 Nanostructure Device Arrays", which is a continuation of Ser. No. 10/388,701 filed Mar. 14, 2003 (U.S. Pat. No. 6,905,655), which claims the priority of U.S. No. 60/366,566 filed Mar. 22, 2002, and which also is a continuation-in-part of U.S. application Ser. No. 10/099,664 (U.S. Pat. No. 7,312,095) filed Mar. 15, 2002; each of which applications are incorporated by reference.

BACKGROUND OF THE INVENTION

1. Field of the Invention

The present invention relates to nanoelectronic devices, and in particular to nanostructured sensor systems for measurement of environmental gases, such as ammonia. Nanostructured sensor embodiments having aspects of the invention have utility in industrial, medical, and personal safety applications, including refrigeration leak detection, environmental management of poultry houses, and the like.

2. Description of Related Art

Ammonia has known toxic effects on both humans and animals even at low exposure levels. For example, occupational health regulations typically set upper limits for acceptable ammonia concentrations for human exposure. The limit in the UK is 25 ppm, in Sweden and Germany the limit is 25 and 20, respectively, for an 8-hour working day. Sweden also has a second limit of 50 ppm for a maximum of 5 minutes exposure.

In addition, ammonia is a common environmental contaminant in poultry houses with important consequences to poultry production. See, for example, I. Estevez, "Ammonia And Poultry Welfare", Poultry Perspectives, Univ. of Maryland, Spring 2002 volume 4, issue 1, which publication is incorporated by reference.

Ammonia in poultry houses is difficult to avoid. Uric acid is excreted by poultry and, unless immediately removed, is decomposed by bacteria growing in the warm, moist conditions present in the poultry house litter. Under these conditions, uric acid is readily oxidized (enzymatic oxidative hydrolysis) to form urea as follows:

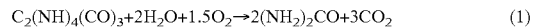

$$C_2(NH)_4(CO)_3 + 2H_2O + 1.5O_2 \rightarrow 2(NH_2)_2CO + 3CO_2 \quad (1)$$

Urea in turn is readily decomposed to form ammonia (hydrolysis by urease) as follows:

$$(NH_2)_2CO + H_2O \rightarrow 2NH_3 + CO_2 \quad (2)$$

The combination of ammonia and wet litter is responsible for a large number of health- and density-related welfare problems in poultry, for example, the occurrence of ascites, gastrointestinal irritation, and respiratory diseases is correlated with high levels of ammonia, as shown in TABLE 1.

TABLE 1

Effect of ammonia levels on poultry health

| Level (ppm) | Effects |
|---|---|
| 10 | Trachea irritation, susceptible to bacterial infections. |
| 20 | Increased rate of infection by Newcastle disease. |
| 25-75 | Impaired growth rate and feed conversion, reduced final body weight. |
| 25-50 | Air sac inflammation |

TABLE 1-continued

Effect of ammonia levels on poultry health

| Level (ppm) | Effects |
|---|---|
| 50 | Increased levels of keratoconjunctivitis. |
| 100 | Increased chick mortality. |

In addition to the animal welfare consequences of the pain and stress of ammonia related pathologies, ammonia levels above about 25-50 ppm have an important affect on growth rate and feed conversion performance. See B. Lott, "Will ammonia really hurt broiler performance?", Chicken Talk, Mississippi State University Extension, Information sheet No. 1639, 2003, which publication is incorporated by reference. It is believed that ammonia levels have a greater impact than behavioral factors in depressing poultry growth at high rearing densities (TABLE 2).

TABLE 2

Effect of ammonia on average body weight of males at 7 weeks age.

| Ammonia (ppm) | 4 weeks (lb) | 7 weeks (lb) |
|---|---|---|
| 0 | 2.99 | 6.74 |
| 25 | 2.95 | 6.55 |
| 50 | 2.41 | 6.24 |
| 75 | 2.47 | 6.23 |

Note that the effects of ammonia are highly dependent on exposure time. Therefore any effect demonstrated at rather high concentrations is likely to be present at much lower concentrations with longer exposure times. The cumulative effect of reduction in poultry growth and feed conversion due to environmental ammonia is a major economic burden on the poultry industry.

While ammonia levels may be partially controlled by attention to poultry diet, watering equipment, absorbent litter, and the like, adequate ventilation control is a necessary component of ammonia level management, as well as for temperature and humidity control. U.S. Pat. No. 5,407,129 issued to Carey et al. describes systems and methods for environmental control of poultry houses, and suggests that ammonia sensors may be included in such systems, which patent is incorporated by reference. However, in practice, systems have not been introduced into the poultry industry that use measurement of ammonia as a primary control variable, and instead typically seek to control ammonia indirectly by monitoring and controlling humidity and temperature.

A variety of different techniques for ammonia sensing are available for sensing ammonia, but generally suffer from one disadvantage or another. Colorimetric indicators or sensing paper do not provide an electronic signal suitable for feedback control systems. Metal-oxide and catalytic metal detectors have generally low selectivity, drift and a high operating temperatures (~400-600 C). Optical gas sensors are generally large, expensive, and slow in response. Conducting polymer detectors have irreversible reactions, limiting their utility.

Current electrochemical sensors for ammonia have an electrolyte component that is consumed as the sensor is exposed to ammonia, thereby limiting service life, except in very low level exposure. The sensor life rating is thus in terms of "exposure time at concentration". For example, for a sensor rating of 1000 ppm-day, an exposure to 50 ppm of ammonia (realistic level for poultry houses) for 20 days will completely exhaust the electrolyte.

What is needed is a low-cost, compact electronic sensor with dependable service life, stable calibration and high selectivity, to provide a practical ammonia sensor for medical, industrial and personal safety applications. In particular, there is a need for such sensors for environmental management of poultry houses and other livestock enclosures.

SUMMARY OF THE INVENTION

Exemplary embodiments of nanoelectronic sensors having aspects of the invention have a conductive (e.g., semiconducting) nanostructured element, the nanostructured element comprising a nanostructured material or "nanostructure". As used herein, the terms "nanostructure" or "nanostructured material" include a particulate or macromolecular entities having at least one dimension less than about 100 nm. The nanostructured material or nanostructure may include single or multiple-wall carbon nanotubes, nanoparticles, nanowires, nanofibers, nanorods, nanospheres, nanohorns or the like, or mixtures of these. Additionally, nanostructures may self-assemble to form composite structures, such as ropes, bundles, or other stable aggregations. Although the principal examples include one or more carbon nanotubes, the nanostructures may comprise boron, boron nitride, and carbon boron nitride, silicon, germanium, gallium nitride, zinc oxide, indium phosphide, molybdenum disulphide, silver, or other suitable materials.

A preferred nanostructured material for employment in nanoelectronic sensors is the carbon nanotube. Nanotubes were first reported in 1993 by S Iijima and have been the subject of intense research since. Single walled nanotubes (SWNTs) are characterized by strong covalent bonding, a unique one-dimensional structure, and exceptionally high tensile strength, high resilience, metallic to semiconducting electronic properties, high current carrying capacity, and extreme sensitivity to perturbations caused by charged species in proximity to the nanotube surface. Elements based on nanostructures such carbon nanotubes (CNT) have unique electrical characteristics, and their sensitivity to environmental changes can modulate the surface energies of the CNT, and can measurably change electrical properties, such as resistance, conductivity, transistor characteristics, capacitance or impedance, and the like. Certain exemplary embodiments having aspects of the invention include single-walled carbon nanotubes (SWNTs) as semiconducting or conducting elements.

Embodiments of sensors may comprise a substrate and a nanostructured element disposed adjacent the substrate. Such nanostructured elements may comprise single or pluralities of discrete parallel elements (e.g. CNTs). For many applications, however, it is advantageous to employ nanostructured elements comprising a film, mat, array or network of semiconducting or conducting nanotubes (or other nanostructures) substantially randomly distributed adjacent a substrate, conductivity being maintained by interconnections between nanotubes. In examples including a substrate configured to have a generally planar form, the nanostructured element may comprise a generally planar layer or coating arranged parallel to the substrate surface. In alternative examples including a substrate configured to have a curved surface shape, such as a rod, or tube-like form, the nanostructured element may comprise a layer or coating arranged to have a similar shape adjacent the substrate.

One or more conductive elements, contacts or electrodes may be disposed adjacent to the nanostructured element so as to communicate electrically with the nanostructured element.

Nanostructured materials comprising a nanostructured element may be non-functionalized, or may functionalized to alter properties. In some embodiments, a nanoelectronic sensor may include a recognition material, layer or coating disposed in association with the nanostructured element, wherein the recognition material may be configured to influence the response of the sensor to an analyte of interest (e.g., increase sensitivity, response rate, or the like) and/or may be configured to influence the response of the sensor to the operating environment (e.g., increase selectivity, reduce interference or contamination, or the like).

For example, functionalization material reactive with $NH_3$ may be disposed on a sensor, for example, on a nanotube. Recognition layers that preserve the semi-conductive or conductive properties may be selected from noncovalent materials, for example, polymer coatings. In certain examples, a recognition material may be isolated from the nanostructure by an insulating coating, such as an ALD dialectic material. Gate electrodes, reference electrodes or other counter electrodes may be included, e.g., for transistor measurements or capacitance measurements of sensor properties.

Certain exemplary embodiments of sensors including nanostructured elements (nanoelectronic sensor or nanosensor) are described in parent application Ser. No. 10/940,324 (published US 2005-0129,573), which is incorporated by reference. Nanosensors having aspects of the invention may be configured for the measurement of analytes, for example ammonia ($NH_3$) present in environmental air. An $NH_3$ sensor may be connected to an electrical circuit, which will respond to changes in $NH_3$ concentration in the ambient sensor environment.

In certain examples, a single substrate sheet, surface or chip may include a plurality of sensors, capable of one or more analytes. Much of the signal processing may be built into the sensor board, requiring only simple and inexpensive external instrumentation for display and data logging, so as to provide a fully calibrated, packaged gas sensor. Alternative embodiments having aspects of the invention include systems configured to include multiplexed assays on a single sensor platform or chip, microprocessors and/or wireless transceivers, permitting convenient recordation and analysis of measurement histories and/or remote monitoring. The output is digital so electronic filtering and post processing may be used to eliminate extraneous noise, if need be. See, for example, U.S. patent application Ser. No. 11/111,121 filed Apr. 20, 2005 entitled "Remotely communicating, battery-powered nanostructure sensor devices"; which is incorporated by reference.

Alternative embodiments having aspects of the invention are configured for detection of analytes employing nanostructured sensor elements configured as one or more alternative types of electronic devices, such as capacitive sensors, resistive sensors, impedance sensors, field effect transistor sensors, and the like, or combinations thereof. Two or more such measurement strategies in a may be included in a sensor device so as to provide orthogonal measurements that increase accuracy and/or sensitivity. Alternative embodiments have functionalization groups or material associated with the nanostructured element so as to provide sensitive, selective analyte response.

One embodiment of a nanosensor having aspects of the invention comprises: a substrate; a nanostructured element disposed adjacent the substrate; one or more conducting elements in electrical communication with the first nanostructure; and at least one functionalization operatively associated with the nanostructured element, the at least one functionalization configured to provide sensitivity for the analyte of interest. Alternative functionalization materials include a range of organic and inorganic materials. A preferred embodiment includes a network of carbon nanotubes disposed adjacent the substrate and functionalized for sensitivity to ammonia. A number of alternative structures and functionalization schemes are described more particularly in the description below and the claims herein.

An alternative embodiment of a nanosensor having aspects of the invention comprises: a substrate, the substrate including a generally sheet-like base material and at least one conductor formed on a surface of the substrate; a network of nanostructures deposited on the substrate so as to contact the at least one conductor formation, the network being deposited on the substrate subsequent to the forming of the at least one conductor; and a recognition material disposed in associated with the network of nanostructures, the recognition material configured to interact with the analyte of interest. In certain examples, the substrate comprises a flexible polymeric material, and wherein the network of nanostructures includes carbon nanotubes deposited upon the substrate from a liquid suspension. In other examples, a recognition material is associated with the nanotubes prior to the deposition of the nanotubes from liquid suspension. A number of alternative structures, and functionalization schemes are described more particularly in the description below and the claims herein.

An embodiment of an integrated sensor system having aspects of the invention comprises: a nanosensor as described above and configured to expose at least a portion of the network and associated functionalization to a sample, and further comprising a contact in communication with the at least one conducting element, the contact exposed on the sensor surface. The embodiment further comprises a sensor socket, including: a body configured to engage and mount the sensor; at least one pin configured to electrically communicate with at least the contact when the sensor is mounted in the socket, the pin configured to communicate at least one signal to measurement circuitry; and an opening configured to provide that the portion of the network and associated functionalization communicates with the sample. In preferred alternatives the sensor is functionalized for sensitivity to ammonia and may be disposable. A number of alternative structures and functionalization schemes are described more particularly in the description below and the claims herein.

One embodiment of a control system for regulating the internal environment having aspects of the invention comprises, a sensor as described above; and a processor in communication with the sensor so as to receive at least one signal indicative of a concentration of the analyte of interest, the processor configured to send at least a command signal to an environmental actuator in response to the at least one signal, the command suited to cause the environmental actuator to control the concentration of the analyte of interest in the enclosed volume. In preferred alternatives the sensor is functionalized for sensitivity to ammonia and may be disposable. A number of alternative structures and functionalization schemes are described more particularly in the description below and the claims herein.

One embodiment of a personnel safety badge having aspects of the invention comprises: a badge body, configured to be worn by the user; a sensor as described above disposed adjacent to the body and configured to measure the analyte of interest; a processor disposed adjacent to the body and in communication with the sensor so as to receive at least one signal indicative of a concentration of the analyte of interest; a power source disposed adjacent to the body and in communication with the processor; and at least one warning output device disposed adjacent to the body, in communication with the processor, and produce at least one communication to the user in response to a concentration of the analyte of interest in the environment of a user.

One method embodiment for dynamic sensor operation having aspects of the invention comprises: (a) selectively exposing at least a portion of a sensor to the environment so that the sensor portion is exposed only intermittently; and (b) dynamically sampling a response signal output from the sensor so as to determine the presence or concentration of the analyte of by analysis of the dynamically sampled signal. A number of alternative operational steps are described more particularly in the description below and the claims herein.

BRIEF DESCRIPTION OF THE DRAWINGS

The following is a list which summarizes the drawings and figures herein:

FIG. 1 is a cross-sectional diagram which illustrates an exemplary electronic sensing device for detecting an analyte, configured in this example as a NTFET.

FIG. 2 are photographic views of a sensor system such as shown in FIG. 1, wherein views (a-c) include SEM images showing (a) showing the layout of interdigitated source and drain contacts S, D, (b) showing an enlarged detail of a nanotube network N and the contacts S, D, and (c) showing an enlarged detail of the margin of network N. View (d) shows an example of a sensor device mounted in a conventional electronic device package.

FIG. 5A shows the response of both capacitance signals and resistance signals to samples of isoflurane in air.

FIG. 5B shows the response of both capacitance signals and resistance signals to samples of halothane in air.

FIGS. 8A-8C illustrate alternative embodiments of sensors having solution deposited nanotube networks, wherein:

FIG. 8A shows a sensor in which a recognition layer is applied following deposition of nanotube film;

FIG. 8B shows a sensor in which a layer of recognition material is deposited upon the substrate prior to application of a nanotube film 2; and FIG. 8C shows a sensor which includes a layer of pre-functionalized nanotubes without a distinct recognition layer.

FIGS. 13A-13E illustrate alternative embodiments of sensors having aspects of the invention and including nanotube networks fabricated by deposition of a solution upon flexible substrates with pre-patterned conductor traces, wherein:

FIG. 13A shows an alternative sensor including a gate dielectric and gate electrode;

FIG. 13B shows a sensor including a plurality of distinct pairs of pre-patterned traces having differently functionalized nanotube networks;

FIG. 13C shows a sensor generally similar to that shown in FIG. 9, and having additional layers for conditioning the sample;

FIG. 13D shows a sensor configured as a capacitance sensor; and

FIG. 13E shows alternative embodiment of a capacitance sensor.

FIGS. 14A-14E illustrate an exemplary embodiment of a sensor system having aspects of the invention, wherein:

FIG. 14A shows a sensor generally similar to the embodiment of FIG. 9 configured as a disposable sensor;

FIG. 14B shows a sensor mounting socket suitable for the sensor of FIG. 14A;

FIG. 14C shows the sensor of FIG. 14A as sealed in a "blister pack" package; and FIG. 14D shows the sensor of FIG. 14A as mounted in the socket of FIG. 14C.

DETAILED DESCRIPTION OF THE PREFERRED EMBODIMENT

A. Exemplary Nanosensor Architecture

Figure 3A:
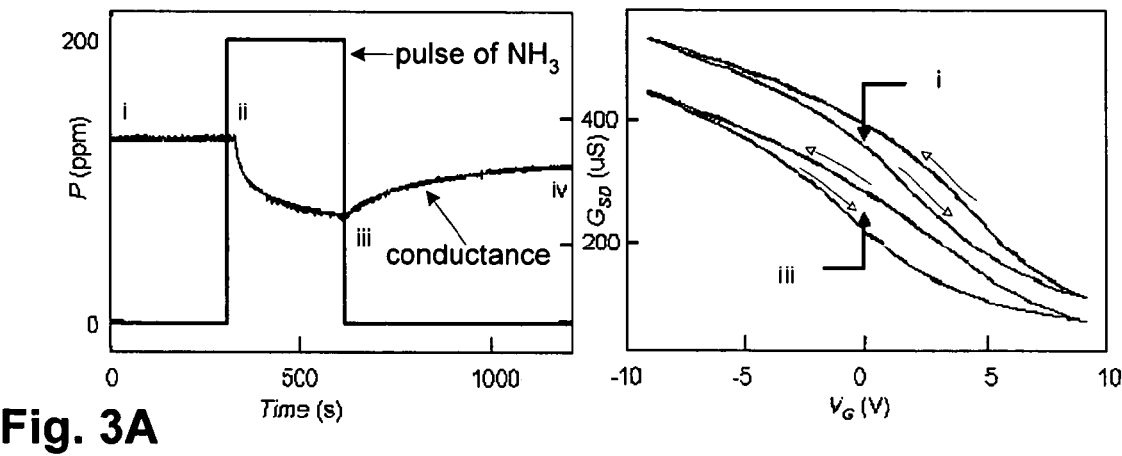
FIG. 3A shows the device characteristics for a transistor device (NTFET) embodiment without additional functionalization (bare nanotubes) to a pulse of 200 ppm ammonia.

FIG. 1. shows an exemplary electronic sensing device 100 having aspects of the invention, for detecting an analyte 101 (e.g., inorganic species such as $NH_3$, $CO_2$, $H_2S$, NO and the like; organic compounds such as glucose, ethanol and the like; biomolecules such as DNA, globular proteins and the like). A number of alternative sensor device architectures and operating modes are possible, and may be employed alone or in combinations without departing from the spirit of the invention. In the example of FIG. 1, sensing device 100 includes a nanostructure sensor 102 configured for convenient transconductance measurements, as well as other properties. Sensor 102 comprises a substrate 104.

Sensor 102 comprises a conductive (e.g., semiconductive) nanostructured element configured to include a channel, coating or layer 106 and comprising a nanostructured material (e.g., one or more conducting or semiconducting nanotubes, nanorods, nanowires and/or nanoparticles; a film, mat or network of nanotubes; combinations of these; or the like). The nanostructured element (layer or channel 106) may be disposed adjacent the substrate 104. Channel or layer 106 may contact the substrate as shown, or in the alternative, may be spaced a distance away from the substrate, with or without a layer of intervening material. In a preferred embodiment, layer 106 comprises an interconnecting network including a plurality of semiconducting single-walled carbon nanotubes (SWNTs).

One or more conductor elements, contacts or electrodes 110, 112 may be disposed over the substrate and electrically connected to channel or layer 106. In the example shown in FIG. 1, the device 100 is configured to facilitate measurements of transconductance properties of channel 106 as influenced or modulated by a constant or variable gate voltage Vg, in this case by employment of substrate 104 as a gate electrode. However, alternative configurations are useful (see discussion of FIG. 3).

Elements 110, 112 may comprise metal electrodes in contact with conducting channel 106. In the alternative, a conductive or semi-conducting material (not shown) may be interposed between contacts 110, 112 and conducting channel 106. Contacts 110, 112 may comprise source and drain electrodes, respectively, upon application of a source-drain voltage Vsd. The voltage or polarity of source 110 relative to drain 112 may be variable, e.g., the applied voltage may be DC, AC, pulsed, or variable. In an embodiment of the invention, the applied voltage is a DC voltage.

In an embodiment of the invention, conducting channel 106 may comprise a plurality of carbon nanotubes forming a mesh, film or network. Such a network may be formed by various suitable methods. One suitable approach may comprise forming an interconnecting network of single-wall carbon nanotubes directly upon the substrate, such as by reacting vapors in the presence of a catalyst or growth promoter disposed upon the substrate. For example, single-walled nanotube networks can be grown on silicon or other substrates by chemical vapor deposition from iron-containing catalyst nanoparticles with methane/hydrogen gas mixture at about 900 deg. C. Advantageously, the use of highly dispersed catalyst or growth-promoter for nanostructures permits a network of nanotubes of controlled diameter and wall structure to be formed in a substantially random and unclumped orientation with respect to one another, distributed substantially evenly at a selected mean density over a selected portion of the substrate.

Alternatively, a nanotube network may be deposited on a device substrate by spray deposition and the like. For example, single wall carbon nanotubes (SWNTs) and/or other nanoparticles may be suspended in a suitable fluid solvent, and sprayed, printed or otherwise deposited in a substrate. The SWNTs or other nanoparticles may optionally have additional functionalization groups, purification and/or other pre-deposition processing. For example SWNTs functionalized with poly m-aminobenzene sulfonic acid (PABS) show hydrophilic properties and may be dispersed in aqueous solutions.

One or more conductive traces or electrodes may be deposited after deposition, or alternatively, the substrate may include pre-patterned electrodes or traces exposed on the substrate surface. Similarly, alternative embodiments may have a gate electrode and a source electrode supported on a single substrate. The substrate may include a flat, sheet-like portion, although one skilled in the art will appreciate that geometric variations of substrate configurations (rods, tubes or the like) may be employed without departing from the spirit of the inventions.

The density of a network of nanotubes (or other nanostructure elements) may be adjusted to achieve a selected conductivity in an electrically continuous network via interconnections between adjacent nanotubes (e.g., a CNT film of density close to but greater than the percolation limit). For example, this may be achieved through controlled CVD conditions (e.g., catalyst particle density, deposition environment, duration, or the like); by controlled flow through a filter membrane (see L. Hu et al., "Percolation in Transparent and Conducting Carbon Nanotube Networks", Nano Letters (2004), 4, 12, 2513-17, which is incorporated by reference), by controlled deposition from a fluid carrier (e.g., spray deposition); or the like.

In a spray-deposition example, multiple light, uniform spray steps may be performed (e.g., with drying and resistance testing between spray steps) until the network sheet resistance reaches a target value (implying a target network density and conductivity). In one example, P2-SWNTs produced by Carbon Solutions, Inc of Riverside, Calif. were spray-deposited on a portion of a PET sheet substrate with pre-patterned traces until a sheet resistance about 1 kΩ was reached.

See also the methods for making nanotube networks as well as additional device and substrate alternatives as described the following patent applications, each of which is incorporated by reference: U.S. patent application Ser. No. 10/177,929 (now abandoned) filed Jun. 21, 2002 entitled "Dispersed Growth Of Nanotubes On. A Substrate", (PCT equivalent published as W004-040,671); U.S. application Ser. No. 10/846,072 (U.S. Pat. No. 7,956,525) filed May 14, 2004, 15 entitled "Flexible nanotube transistors" (published 2005-0184,641); U.S. patent application Ser. No. 11/274,747 (now abandoned) filed Nov. 14, 2006 (published 2007-0208243) entitled "Nanoe/ectronic Glucose Sensors"; and U.S. patent application Ser. No. 60/748,834, filed Dec. 9, 2005, entitled "Nanoelectronic Sensors Having Substrates With Pre-Patterned Electrodes, And Environmental Ammonia Control System".

Similar methods of making and depositing alternative nanostructures may be employed, so as to configure a nanostructured elements comprising a networks or film of, for example, nanospheres, nanocages, nanococoons, nanofibers, nanowires, nanoropes and nanorods, or mixtures thereof, having compositions including carbon, boron, boron nitride, and carbon boron nitride, silicon, germanium, gallium nitride, zinc oxide, indium phosphide, molybdenum disulphide, and silver.

In the example of FIG. 1, the device 100 may be operated as a gate-controlled field effect transistor, with sensor 102 further comprising a gate electrode 114. Such a device is referred to herein as a nanotube field effect transistor or NTFET. Gate 114 may comprise a base portion of substrate 104, such as a doped-silicon wafer material isolated from contacts 110, 112 and channel 106 by a dielectric layer 116, so as to permit a capacitance to be created by an applied gate voltage Vg. For example, the substrate 104 may comprise a silicon back gate 114, isolated by a dielectric layer 116 comprising $SiO_2$. Alternatively gate 114 may include a separate counter electrode, liquid gate or the like.

Sensor 102 may further comprise a layer of inhibiting or passivation material 118 covering regions adjacent to the connections between the conductive elements 110, 112 and conducting channel 106. The inhibiting material may be impermeable to at least one chemical species, such as to the analyte 101 or to environmental materials such as water or other solvents, oxygen, nitrogen, and the like. The inhibiting material 118 may comprise a passivation material as known in the art, such as silicon dioxide, aluminum oxide, silicon nitride, or other suitable material. Further details concerning the use of inhibiting materials in a NTFET are described in prior co-invented U.S. Pat. No. 6,894,359 entitled "Sensitivity Control For Nanotube Sensors" which is incorporated by reference herein.

Device 100 may further comprise suitable circuitry in communication with sensor elements to perform electrical measurements. For example, a conventional power source may supply a source drain voltage Vsd (113) between contacts 110, 112. Measurements via the sensor device 100 may be carried out by suitable measurement circuitry represented schematically by meter 122 connected between contacts 110, 112. In embodiments including a gate electrode 114, a conventional power source 124 may be connected to provide a selected or controllable gate voltage Vg. Device 100 may include one or more electrical supplies and/or a signal control and processing unit (not shown) as known in the art, in communication with the sensor 102.

Optionally, device 100 may comprise a plurality of sensors like sensor 102 disposed in a pattern or array, such as described in prior application Ser. No. 10/388,701 filed Mar. 14, 2003 entitled "Modification Of Selectivity For Sensing For Nanostructure Device Arrays" (now published as US 2003-0175161), which is incorporated by reference herein. Each device in the array may be functionalized with identical or different functionalization. Identical device in an array can be useful in order to multiplex the measurement to improve the signal/noise ratio or increase the robustness of the device by making redundancy. Different functionalization may be useful for providing differential sensitivity so as to permit measurement of a profile of different responses to analytes.

The substrate 104 may be insulating, or on the alternative, may comprise a layered structure, having a base 114 and a separate dielectric layer 116 disposed to isolate the contacts 110, 112 and channel 106 from the substrate base 114. The substrate 104 may comprise a rigid or flexible material, which may be conducting, semiconducting or dielectric. Substrate 104 may comprise a monolithic structure, or a multilayer or other composite structure having constituents of different properties and compositions. For example, in an embodiment of the invention, the substrate 104 may comprise a silicon wafer doped so as to function as a back gate electrode 114. The wafer being coated with intermediate diffusion barrier of $Si_3N_4$ and an upper dielectric layer of $SiO_2$. Optionally, additional electronic elements may be integrated into the substrate for various purposes, such as thermistors, heating elements, integrated circuit elements or other elements.

In certain alternative embodiments, the substrate may comprise a flexible insulating polymer, optionally having an underlying gate conductor (such as a flexible conductive polymer composition), as described in application Ser. No. 10/846,072 filed May 14, 2004, which application is incorporated by reference. In further alternative embodiments, the substrate may comprise a polymeric substance coated with nanotube or other nanostructure particles in the in the manner described in U.S. application Ser. No. 11/274,747 filed Nov. 14, 2005, which application is incorporated by reference.

The conducting channel 106 (e.g., a carbon nanotube layer) may be functionalized to produce a sensitivity to one or more target analytes 101. Although nanostructures such as carbon nanotubes may respond to a target analyte through charge transfer or other interaction between the device and the analyte, more generally a sensitivity can be achieved by employing a recognition material 120, also called a functionalization material, that induces a measurable change in the device characteristics upon interaction with a target analyte. In addition or in substitution to the metallic nanoparticle functionalization, of the exemplary embodiments described in detail herein, the functionalization may alternatively include metal oxides, metal salts, polymers, and the like. Likewise, functionalization may include composite nanoparticles, mixtures of materials or the like.

In the exemplary embodiments described in detail herein, the recognition material disposed upon the channel 106 comprises on or more metallic materials. In particular, alternative embodiments of arrays of sensors such as shown in FIG. 1 may be functionalized with a range of materials different catalytic metals to produce cross-sensitive NTFET sensor elements.

FIG. 2 are photographic views (a-d) of a sensor system 100 such as shown in FIG. 1, wherein views (a-c) include SEM images showing (a) showing the layout of interdigitated source and drain contacts S 110 and D 112, (b) showing an enlarged detail of a nanotube network N 106 and the contacts S 110 and D 112, and (c) showing an enlarged detail of the margin of network N 106. View (d) shows an example of a sensor device 100 mounted in a conventional electronic device package 130. Note that the extent of a carbon nanotube network may be conveniently controlled by selective or masked oxidation of nanotubes from peripheral regions of the substrate 104 ("ashing").

The conducting channel 106 (e.g., a carbon nanotube layer) may be functionalized to produce a sensitivity to one or more target analytes 101. Although nanostructures such as carbon nanotubes may respond to a target analyte through charge transfer or other interaction between the device and the analyte, a specific sensitivity may be achieved by employing a recognition material 120, also called a functionalization material, that induces a measurable change in the device characteristics upon interaction with a target analyte.

Device 100 may be packaged in a conventional manner to conveniently permit connection to operating circuitry. FIG. 2, view (d) is a photograph of a sensor device 100 generally similar to that of views (a-c), fabricated on a die of a wafer, and mounted as a chip in a conventional 40 pin CERDIP package using wirebonding techniques. Device 100 may further comprise suitable circuitry in communication with sensor elements to perform electrical measurements. For example, a conventional power source may supply a source-drain voltage (Vsd) between contacts 110, 112. Measurements via the sensor device 100 may be carried out by circuitry represented schematically by meter 122 connected between contacts 110, 112. In embodiments including a gate electrode 114, a conventional power source 124 may be connected to provide a selected or controllable gate voltage (Vg). Device 100 may include one or more electrical supplies and/ or a signal control.

Ammonia detection. A nanotube network device such as is shown in FIG. 2 may be functionalized as an ammonia detector having aspects of the invention, as described in U.S. patent application Ser. No. 10/656,898 filed Sep. 5, 2003 (published 2005-0279,987) entitled "Polymer Recognition Layers For Nanostructure Sensor Devices"; and U.S. patent application Ser. No. 11/541,794, filed Oct. 2, 2006 entitled "Nanosensor Array For Electronic Olfaction", incorporated by reference herein.

A recognition layer (corresponding to 120 in FIG. 1) may be applied to the nanotube network 106 using any suitable method. For example, in an embodiment of the invention, the substrate 104, electrodes 110, 112 and nanotube network 106 were submerged in a solution of poly(ethylene imine) (PEI, average molecular weight ~25,000, Aldrich) at about 20% by weight in methanol. After soaking overnight, they were removed and rinsed with methanol. A thin layer, such as less than 10 nm of PEI coated the exposed portion of nanotube 106 after rinsing. Other suitable polymers, or combinations of polymers, may be substituted for PEI. Other solvents and rinse agents may also be suitable.

FIG. 3A shows the device characteristics for a transistor device (NTFET) embodiment without additional functionalization (bare nanotubes). The left hand plot of FIG. 3A shows the ammonia concentration in ppm and the conductance at initial zero NH3 concentration (i-ii), a sustained pulse of 200 ppm (ii-iii) having a loss of conductance, followed by a recover period of zero ppm (iii-iv). The right hand plot of FIG. 3A shows the variation of conductance as a function of gate voltage (note hysteresis during sweep), the upper curve set representing point (i) prior to ammonia pulse, and the lower curve set representing point (iii) after full response to ammonia pulse, but before recovery. Note that the shape of the device characteristic curve set is generally similar, the response to ammonia being an overall reduction in conductance at both positive and negative gate voltages.

Figure 3B:
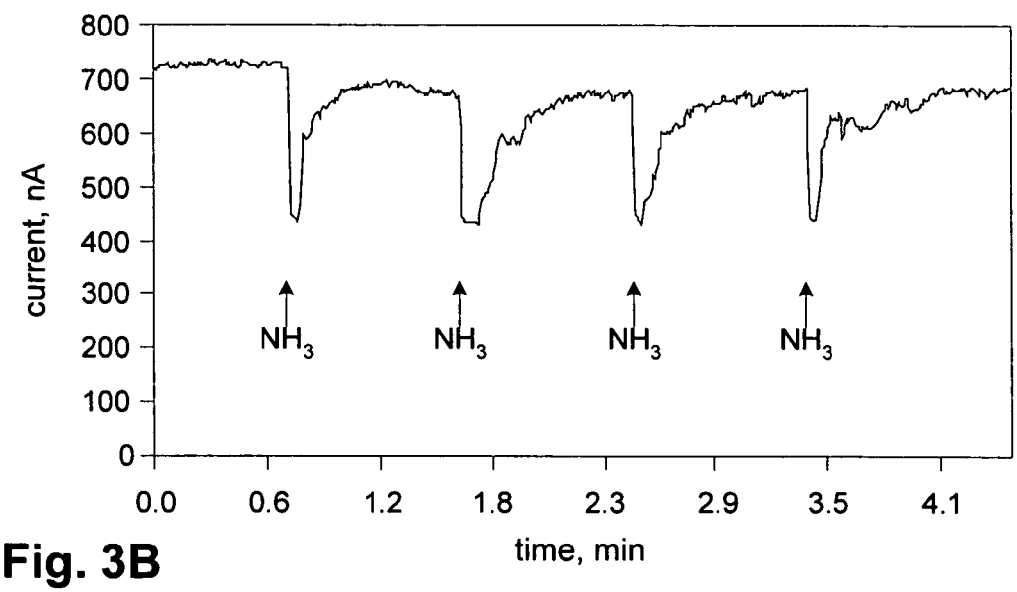
FIG. 3B shows exemplary response of a nanotube device that is not coated with a recognition layer to fluctuating levels of NH3 in a test environment.
Figure 3C:
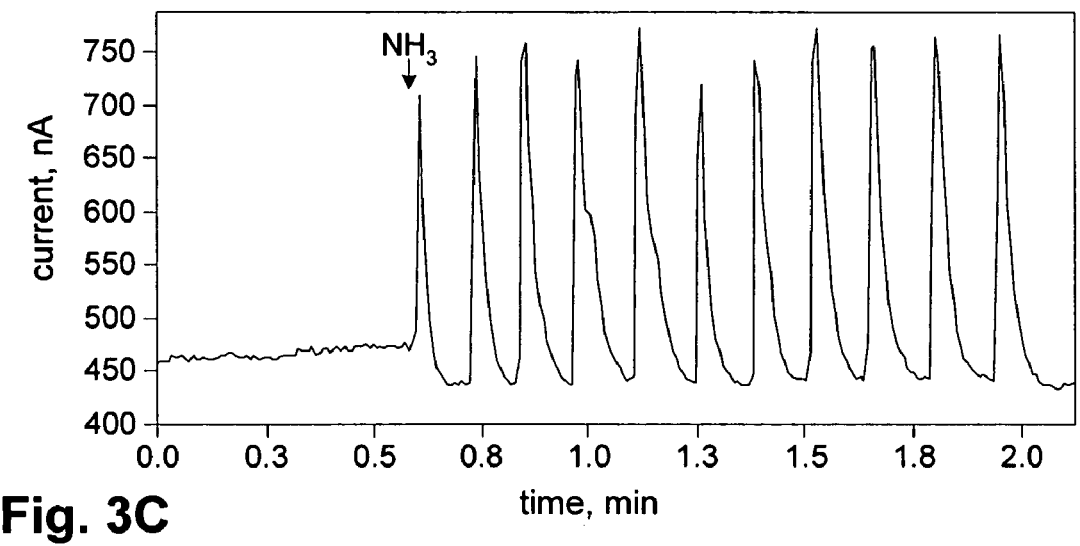
FIG. 3C shows exemplary improved response of a nanotube device coated with a PEI recognition layer to NH3 in the same test environment.

FIGS. 3B and 3C show the response of the non-functionalized device and the PEI functionalized device, respectively, to exposure to pure ammonia gas. It may be seen that functionalization with PEI improved the response of the semiconducting nanostructure device for NH3. As seen in FIG. 3B, the non-functionalized device responds with a modest reduction in current, followed by comparatively slow recovery. In contrast, the response and recovery of the PEI-functionalized ammonia sensor (FIG. 3C) is remarkably fast, and the device responds with a substantial increase in current. Upon exposure to pure ammonia gas the current increases from 400 nA to 800 nA. The measured change in current is dependent on ammonia concentration. When the device was exposed to different concentrations of ammonia in argon, a change in the device conductivity was found to be proportional to ammonia concentration. The response to ammonia is also dependent on a gate voltage. At positive gate, measured current through the PEI-functionalized device is increasing significantly. This is true with or without the functionalization material.

Figure 4:
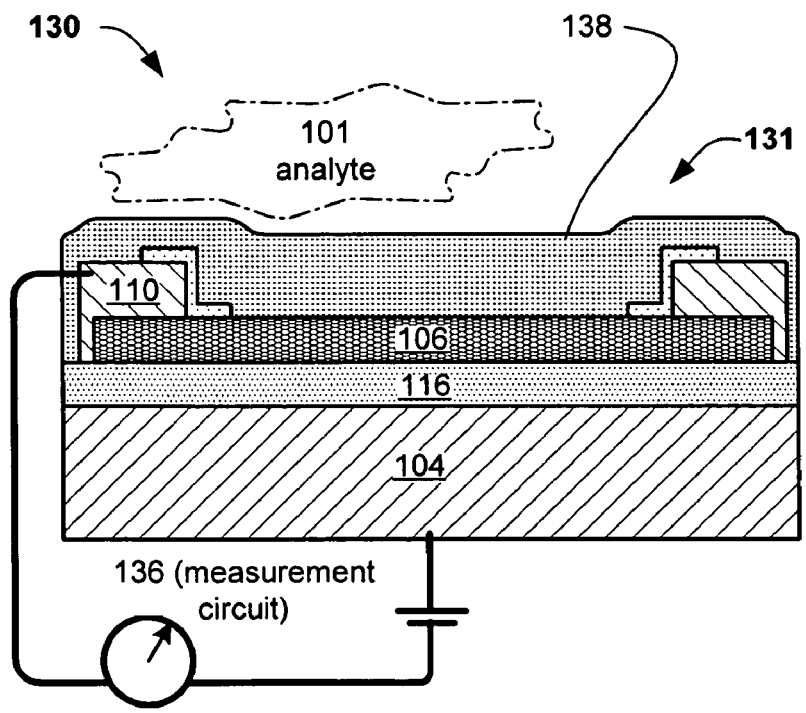
FIG. 4 is a cross-sectional diagram which illustrates an exemplary electronic sensing device, similar in a number of respects to the device of FIG. 1, configured in this example configured for measurement of capacitance and related properties as a signal for detecting an analyte.

Alternative nanosensor architectures. FIG. 4 shows one example of a an exemplary electronic sensing device 130 having aspects of the invention, similar in a number of respects to the device of FIG. 1, configured in this example as a capacitance sensor for detecting an analyte, as further described in commonly invented and assigned U.S. Provisional Applications No. 60/773,138 filed Feb. 13, 2006; No. 60/660,441, filed Mar. 10, 2005; and No. 60/669,126, filed Apr. 6, 2005, each of which is incorporated by reference. Where appropriate, the same reference numerals are used to denote elements which may have commonality of function with respect to FIG. 1. Nanostructured capacitance sensors may be used in conjunction with transconductance sensor modalities, so as to increase specificity, reduce cross sensitivity, and to provide an additional means of sensor calibration.

As shown in FIG. 4, Sensor device 130 includes a nanostructure sensor 131 which includes a conductive nanostructured element configured to include a channel, coating or layer 106 comprising a nanostructured material (see description of example of FIG. 1). In an exemplary embodiment, the nanostructured material includes a carbon nanotube network 106, disposed upon a substrate comprising a dielectric isolation layer 116 disposed upon a base 114, in this example a doped silicon wafer back gate.

The nanotube network 106 is contacted by at least one conductive electrode 110 (in this case having optional passivation on the electrode-nanotube contact region). A conditioning/recognition structure 138 may be included, disposed adjacent network 106 and may included functionalization or recognition material, analyte conditioners (e.g., a filter, selectively permeable polymer, etc.) and the like.

The sensor device 130 further includes at least a capacitance measurement circuit 136 in electrical communication with contact 110 and back gate 114, so as to permit the capacitance and/or impedance of the spaced apart nanotube network/back gate assembly to be readily measured (i.e., the total charge required to be placed on either conductor to create a given voltage potential between conductors, $C=Q/V$).

It should be understood that other capacitor conductors may be substituted for back gate 114 or added to the device 1300 without departing from the spirit of the invention, such as a top gate, liquid gate, a second spaced-apart nanotube network conductor, and the like. Additionally, many alternative functional arrangements of the respective conductors are possible. The capacitance C of the sensor 131 may be calibrated, and compared analytically with the capacitance during exposure to analyte of interest 110. In particular, species having significant dipole moments may act to change the capacitance upon interaction with the nanotube network 106. As shown in FIG. 4, additional functionalization 138 may be included in sensor 131 (e.g., an absorbent filter, a selectively permeable polymer layer, a selectively reactive or binding species, etc., to enhance selectivity, sensitivity and/or signal strength).

Combined conductance and capacitance measurements. Simultaneous conductance and capacitance measurements on a nanostructure sensor element (e.g., a single-walled carbon nanotube (SWNT) network may be used to extract an intrinsic property of molecular adsorbates. From a comparison of FIG. 1 and FIG. 4, it may seen that a single sensor configuration may be combined with circuitry permitting measurements in several modalities from a single sensor. Alternatively, a plurality of differently configured sensors may be employed. Measurements may be made of related properties as well, such as impedance of a sensor having a capacitive circuit architecture below).

For example, adsorbed analytes produce a rapid response in both the capacitance and the conductance of a SWNT network. These responses are caused by a combination of two distinct physiochemical properties of the adsorbates: charge transfer and polarizability. It has been shown that the ratio of the conductance (or resistance) response to the capacitance response is a concentration-independent intrinsic property of a chemical vapor that can assist in its identification. See Eric S. Snow and F. Keith Perkins, "Capacitance and Conductance of Single-Walled Carbon Nanotubes in the Presence of Chemical Vapors", Nano Lett (2005) 5 (12), 2414-2417, which publication is incorporated by reference.

Thus, a sensor system may produce a response which characterizes analyte identity in one output or signal analysis mode, and produce a response which characterizes analyte concentration in another output or signal analysis mode. In one exemplary embodiment having aspects of the invention, a sensor system may include capacitance and resistance measurement/processing circuitry communicating with a nanosensor (e.g., such as in FIG. 1) to determine the identity of an analyte employing a ratio of the resistance and capacitance change upon exposure to an analyte sample, and then determine a concentration of the thus-identified analyte from the capacitance change based on analyte-specific calibration data.

FIGS. 5A and 5B are plots illustrating one example of the use of multiple measurement modalities for analyte detection and discrimination. The measurements represent the response of a sensor having aspects of both FIGS. 1 and 4. In each case, the sensor was exposed to a sequential set of samples of an analyte gas in air, through a graded series of concentrations. The samples are administered in timed pulses of approximately 60 second duration each. The overlay dashed line at each concentration is not a measured value, but an approximated mean level, shown for clarity and convenience. The sensors employed in the examples of FIGS. 5A-5B included a directly-exposed nanotube network, although various functionalization and conditioning layers or materials may optionally be included (see FIG. 4). In each plot, a capacitance response to an exemplary analyte species is shown superimposed upon a signal measuring the simultaneous source-drain resistance, the capacitance units being shown on the left-hand axis, and the resistance units on the right-hand axis.

FIG. 5A shows the response of both capacitance signal resistance signals to samples of an exemplary analyte in air, in this example the anesthetic agent, isoflurane. The response of the device to the analyte in both the capacitance and resistance signals can be seen to be very rapid, with a rapid recovery. The relation of capacitance to isoflurane concentration can be seen to be in the opposite direction, each generally proportional in magnitude to the other. The arrows to the right of the plot illustrate the magnitude and ratios of the respective measurements at a 5% analyte concentration.

FIG. 5B shows the comparable responses of both capacitance signal resistance signals to samples of halothane in air; respectively, plotted in the same manner as FIG. 5A. The arrows to the right of the plot illustrate the magnitude and ratios of the respective measurements at a 5% analyte concentration.

Halothane and isoflurane are chemically similar, have similar properties, but may be distinguished based on the relative magnitude of the responses (e.g., a ratio of ~185 for isoflurane vs. ~169 for halothane). The this ratio may be used to confirm or distinguish the identity of an analyte, and advantageously this may be done in conjunction with the simultaneous measurement of the agent's concentration. Where Vg is the voltage of a substrate gate such as is shown in FIG. 1, the signals of capacitance and conductance (or resistance) may be converted for comparison (e.g., ratio calculation) to normalized values in units of $\Delta Vg$ that represent the change in the substrate gate electrode (counter electrode) voltage required to produce an equivalent change in capacitance AC (or change in resistance $\Delta R$), i.e. $\Delta C^* = \Delta C/(dC/dVg)$ and $\Delta G^* = \Delta R/(dR/dVg)$ where the derivatives are evaluated at Vg=0.

Optional Device Elements. Optionally, a nanosensor device having aspects of the invention may include integrated temperature control elements. Temperature control may be used to control sensor sensitivity, selectivity, and/or recovery time. Thermal control may also be used to carry out analyte-related processes, such as polynucleotide hybridization and denaturization, stringency conditions, PCR, biomolecule conformation changes and the like.

For example, a nanosensor may include ohmic thermal regulation of the nanotubes of the channel, as described in U.S. patent application Ser. No. 10/655,529 filed Sep. 4, 2003 entitled "Improved Sensor Device With Heated Nanostructure", which is incorporated by reference.

In another alternative embodiment, the sensor device may include a microfabricated heater element and a thermal isolation structure, such as a substrate bridge or a suspended membrane. Such components may include temperature feedback sensors, such as thermistors, to assist in automated thermal control, e.g., using a microprocessor, as further described in commonly invented and assigned U.S. application Ser. Nos. 11/488,465 60/700,953, filed Jul. 18, 2006, entitled "Nanoelectronic Sensor With Integral Suspended Micro-Heater", which is incorporated by reference. See also C. Tsamis et al, "Fabrication of suspended porous silicon microhotplates for thermal sensor applications", Physica Status Solidi (a), Vol 197 (2), pp 539-543 (2003); A Tserepi et al, "Fabrication of suspended thermally insulating membranes using front-side micromachining of the Si substrate: characterization of the etching process", J of Micromech. and Microeng, Vol 13, pp 323-329 (2003); A Tserepi et al, "Dry etching of Porous Silicon in High Density Plasmas", Physica Status Solidi (a), Vol 197 (1), pp 163-167 (2003), each of which is incorporated by reference.

B. Exemplary Flexible Substrate Nanosensors

A number of alternative methods of forming a nanostructure network channel (e.g., N in FIG. 1C) may be employed without altering the underlying principal of operation of nanosensors having aspects of the invention. In certain embodiments (e.g., for fabrication condition compatibility), it is advantageous to form a nanotube (or other nanostructure) network on an initial substrate, and subsequently transfer the network to a final device substrate. See for example, the methods described in U.S. patent application Ser. No. 10/846,072, filed May 14, 2004 (published 2005-0184,641), entitled "Flexible Nanotube Transistors", which is incorporated by reference.

Figure 6:
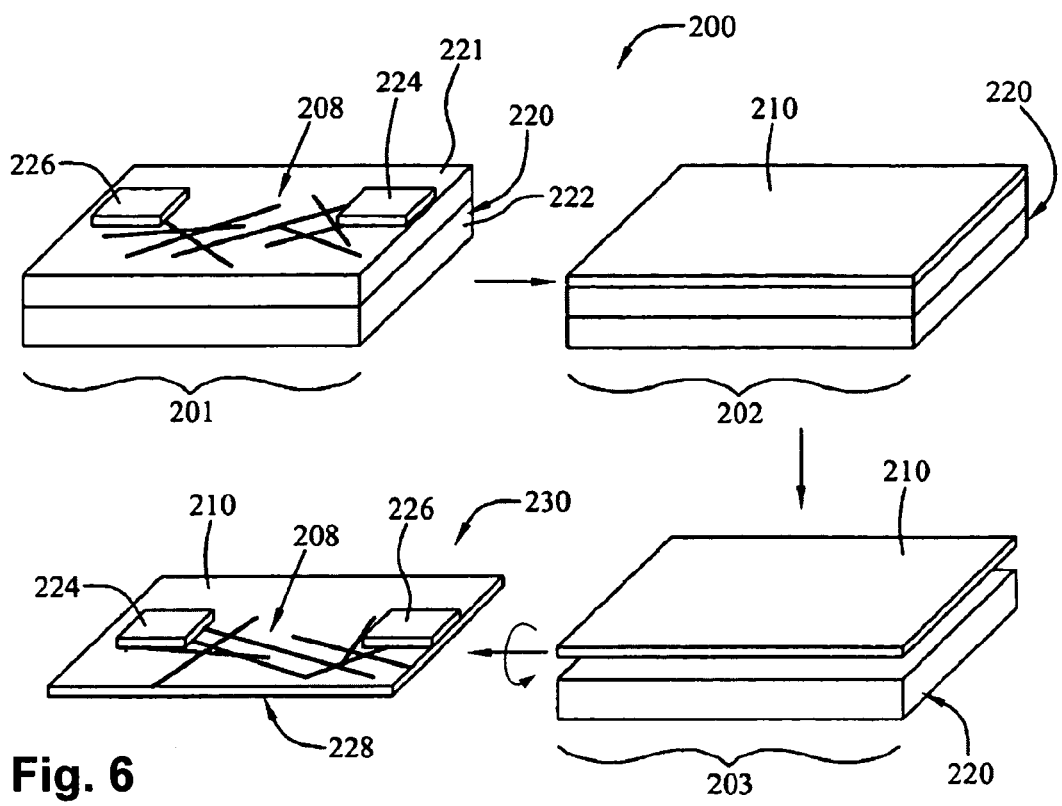
FIG. 6 is a flow diagram showing exemplary steps of a method according to the invention for producing a device including a CVD deposited CNT network and having a polymer substrate.

As shown in FIG. 6 (corresponding to FIG. 2 of the above referenced application Ser. No. 10/846,072) in one alternative method, flexible nanostructure electronic device 200 is formed as follows: Step 201 includes depositing or growing (for example, by chemical vapor deposition) a nanotube film 208 on a rigid substrate 220. Substrate 220 may comprise, for example a silicon material 222 covered by a layer of silicon oxide 221. Optionally, contacts 224, 226 may be formed on the substrate, either before or after the nanotube film is formed. At step 202, nanotube film 208 and substrate 220 may be coated with a flexible substrate layer 210. Flexible substrate layer 210 may comprise any suitable material capable of forming a coating film, for example, a liquid polymer. Other polymers that may be used to effect a conductivity change in nanotubes in response to absorption of target species. Alternative materials for layer 210 may include, for example, those identified in TABLE 3. Such materials may be included in sensors such as are describe herein, alone or in combination, without departing from the spirit of the invention.

TABLE 3

Examples of alternative recognition materials

| | |
|---|---|
| Polyacrylic acid | Polyurethane resin |
| Poly(acrylic acid-co-isooctylacrylate) | Polycarbazole |
| poly(ethylene imine), "PEI" | poly(sulfone) |
| poly(4-vinylphenol) | poly(vinyl acetate) |
| poly(alkyl methacrylate) | poly(vinyl alcohol) |
| poly(a-methylstyrene) | poly(vinyl butyral) |
| poly(caprolactone) | polyacrylamide |
| poly(carbonate bisphenol A) | polyacrylonitrile |
| poly(dimethylsiloxane) | polyaniline |
| poly(ethylene glycol) | polybutadiene |
| poly(ethylene oxide) | polycarbonate |
| poly(ethylenimine) | polyethylene |
| poly(methyl vinyl ether-co-maleic anhydride) | polyoxyethylene |
| poly(N-vinylpyrrolidone) | polypyrrole |
| poly(propylene) | polytetrafluoroethylene |
| poly(styrene) | polythiophene |
| polyvinyl-methyl-amine | Polyvinyl pyridine |
| polyaminostyrene | |
| chitosan | chitosan HCL |
| polyallylamine | polyallylamine HCL |
| poly(diallylamine) | poly(diallylamine) HCL |
| poly(entylene-co-vinyl acetate), ~82% ethylene | poly-(m-aminobenzene sulfonic acid), "PABS" |
| poly(styrene-co-allyl alcohol), ~5.7% hydroxyl | poly(vinyl chloride-co-vinyl acetate), ~10% vinyl acetate |
| poly(styrene-co-maleic anhydride), ~50% styrene | poly(vinylidene chloride-co-acrylonitrile), ~80% vinylidene chloride |
| metalloporphyrin (M-porph) | Poly-L-lysine |
| Alpha-fetoprotein Profile Four (AFP4) | glycerol |
| Poly methyl methacrylate (PMMA) | polyglycerol |
| Nafion NR 50 | Triton 100 and similar surfactants or amphiphilic species |
| metal coatings and nanoparticles, and alloys or mixtures of these: | Fe, V, Au, Pt, Pd, Ag, Ni, Ti, Cr, Cu, Mg, Al, Co,, Zn, Mo, Rh, Sn, W, Pb, Ir, Ru, Os |
| inorganic coatings and/or nanoparticles: | |
| $V_2O_5$ | $WO_3$ |
| $Cu(SO_4)$ | Boric/Boronic acid |
| ZnO | Boron Trichloride |
| $Al_2O_3$ | $ZrO_2$ |
| $Fe_2O_3$ | $CaCl_2$ |

Materials in the functionalization layer may be deposited on the NTFET using various different methods, depending on the material to be deposited. It should be understood that mixtures, alloys and composites of the materials may also be included. For many materials, ALD methodology is known which is suitable for depositing thin, uniform layers or coatings, which may be controlled to deposit on selected portions of a device, and which may be employed to produce mixtures or multi-layer coatings also. Other methods may be employed. For example, inorganic materials, such as sodium carbonate, may be deposited by drop casting from 1 mM solution in light alcohols. The functionalized sensor may then be dried by blowing with nitrogen or other suitable drying agent. Polymeric materials may be deposited by dip coating. A typical procedure may involve soaking of the chip with the carbon nanotube device in 10% polymeric solution in water for 24 hours, rinsing with water several times, and blowing the chip dry with nitrogen. Polymers which are not soluble in aqueous solutions may be spin coated on the chip from their solutions in organic solvents. Values of polymer concentrations and the spin coater's rotation speeds may be optimized for each polymer.

Polymers such as the foregoing may be dissolved and coated on nanostructures in a manner similar to that described for PEI above. Polymer and non-polymer materials other than those listed above may also be useful. It is possible that the exemplary polymer layer acts to cause a selective response by the nanostructure to target species that are selectively absorbed or otherwise interacted with by the polymer layer on the nanostructure. This suggests that a nanostructure sensor may be made to respond selectively to a particular material, by coating it with a polymer or material having a known selective affinity for the desired target. Also, more than one material may be included in a target group by combining polymers with different affinities. The polymer layer may be modified to produce different effects. For example, part of the nanotube or other nanostructure may be masked during a coating process for the polymer layer. After the polymer layer is applied, the masking layer may be stripped away, leaving a discontinuous polymer layer on the nanotube. Using a similar process, different polymers may be deposited at different places along a nanostructure.

The polymer or other recognition material should be selected to provide the electrical and mechanical properties that are desired for the substrate of the device to be formed. The polymer 210 may be deposited as a liquid layer, and then cured, hardened, or otherwise solidified to provide the desired substrate material.

At step 203, rigid substrate 220 is removed from substrate 210, for example, by dissolving the substrate in a suitable etching agent. Optionally, one or more electrodes (not shown) may be formed on the exposed surface of substrate layer 210, either before or after it is removed from the rigid substrate. For example, a gate electrode (not shown at 203) may be placed opposite to the nanotube film 208. Turning substrate 210 over should yield a device 230 as shown at the lower left of FIG. 6 (shown rotated 180 degrees relative to its position at 201). The device 230 may comprise source and drain electrodes 224, 226, nanotube network 208 connecting the source and drain, and a gate electrode 228 on the opposite side of dielectric flexible substrate layer 210.

A nanotube network was grown by chemical vapor deposition on a silicon substrate with a 200 nm silicon oxide coating, as described in U.S. patent application Ser. No. 10/177,929, filed Jun. 21, 2002 by Gabriel et al., which is hereby incorporated by reference, in its entirety. Then the silicon substrate with the network was patterned with optical lithography, and a liftoff process, to form 100.mu.m square metal contacts. The metal contacts comprised a 3.5 nm thick titanium film covered by a 50 nm thick gold film. After liftoff, the silicon substrate with network and metal contacts was spin-coated with polyimide (HD 2610, 500 rpm). The silicon substrate was heated at 90 deg C. for 10 minutes, 120 deg C. for 5 minutes, and 200 deg C. for 30 minutes to cure the polyimide. Finally, the silicon substrate was immersed in 10% hydrofluoric acid (HF) for 8 hours. The polyimide films, floating freely in the HF solution, were removed and rinsed with deionized water.

Figure 7:
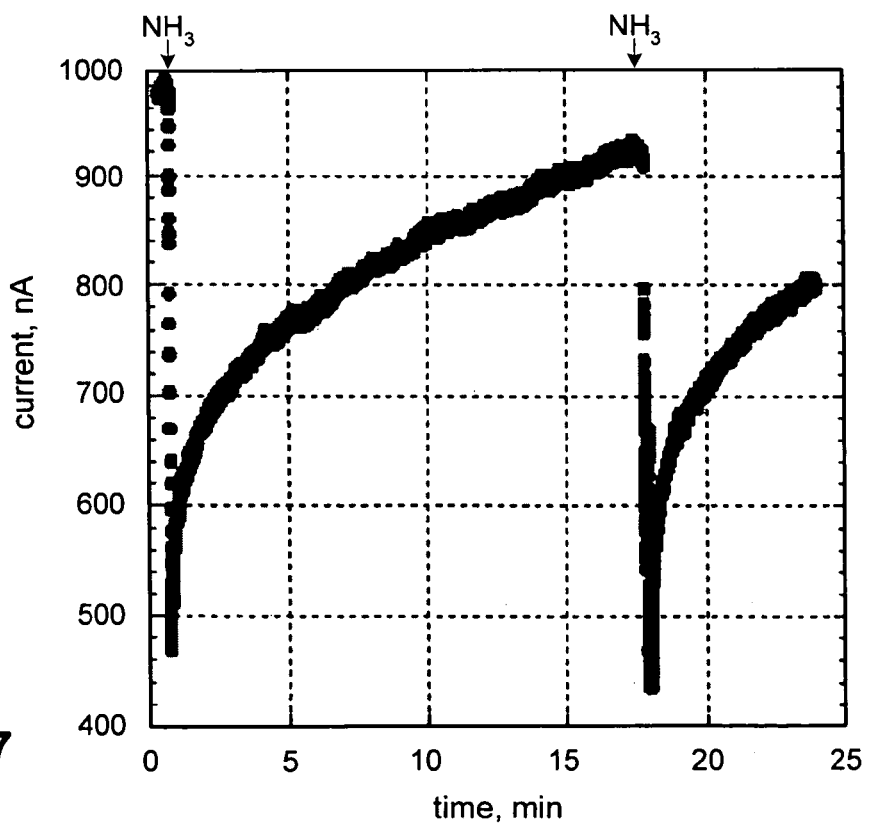
FIG. 7 is a plot showing the response to ammonia of the sensor of FIG. 6.

FIG. 7 shows the NH3 sensing capabilities of a nanosensor embodiment having aspects of the invention, in this case a sensor constructed by the method of FIG. 6 Introduction of NH3 to a test chamber caused a rapid and easily measured change in conductivity of the device.

C. Exemplary Solution Deposition Nanosensors

Solution Deposition Nanoparticle Network. In an alternative, the nanostructure conducting layer comprising an interconnecting network of nanostructures may be formed by deposition from a solution or suspension of nanostructures, such as a solution of dispersed carbon nanotubes. See for example, the methods described in U.S. patent application Ser. No. 10/846,072, filed May 14, 2004 (published 2005-0184,641), entitled "Flexible Nanotube Transistors", which is incorporated by reference. Such methods as spin coating, spray deposition, dip coating and ink-jet printing may be employed to deposit the solution or suspension of nanostructures.

In certain embodiments, a micro-porous filter, membrane or substrate may be employed in deposition of a nanotube (or other nanoparticle) network channel from suspension or solution. A porous substrate can accelerate deposition by removing solvent so as to minimize "clumping", and can assist in controlling deposition density. The deposition may be carried out by capillary absorption, or using suction or vacuum deposition across the porous substrate or membrane, as described in the above referenced application Ser. No. 10/846,072 (e.g., see description of FIG. 3 and Example B of that application); in U.S. Provisional Application No. 60/639,954 filed Dec. 28, 2004 entitled "Nanotube Network-On-Top Architecture For Biosensor"; and in L. Hu et al., Percolation in Transparent and Conducting Carbon Nanotube Networks, Nano Letters (2004), 4, 12, 2513-17, each of which application and publication is incorporated herein by reference. The network thus formed may be separated from the deposition membrane using a method such as membrane dissolution or transfer bonding, and included in a sensor device structure as a conducting channel (e.g., disposed on a device substrate, contact grid, or the like).

Alternatively, a nanotube (or other nanoparticle) network deposited on a micro-porous substrate may be included in a sensor device as disposed upon the deposition substrate or membrane. This arrangement may simplify fabrication, and has the advantage of permitting analyte media flow perpendicularly through the pores of the device substrate, as further described in commonly invented and assigned U.S. Provisional Application No. 60/669,126, filed Apr. 6, 2005, entitled "Systems Having Integrated Cell Membranes And Nanoelectronics Devices, And Nano-Capacitive Biomolecule Sensors, which is incorporated by reference.

Figure 8A:
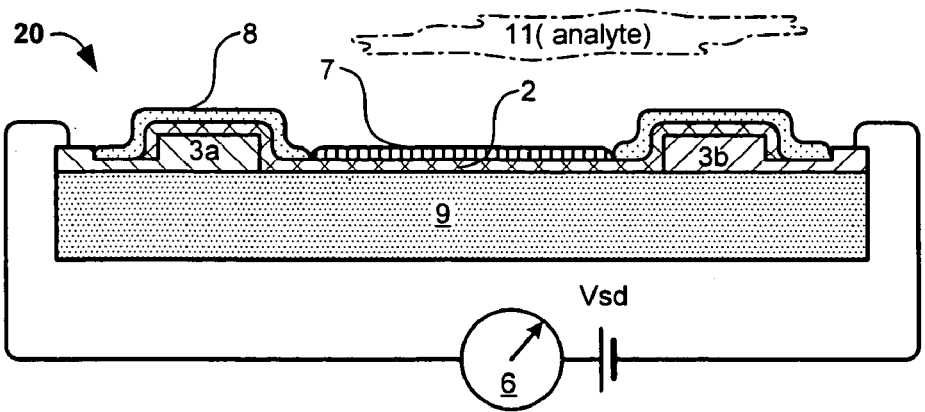

FIG. 8A is a diagram of an alternative exemplary embodiment of a nanosensor 20 having aspects to the invention, including a network of carbon nanotubes. Sensor 20 comprises a substrate 9, which may comprise a flexible sheet-like material such a polyester polymer (e.g., PET sheet). One or more electrodes (3a and 3b are shown) are arranged on the substrate. The electrode 3 may comprise a metal, or may be formed from a paste or ink-like composition, such as carbon, graphite, conductive polymer, metallic ink compositions, and the like.

A nanostructure layer 2 (in this example a film including SWNTs) is deposited contacting the electrodes 3a (and 3b in this example). Preferably the nanostructure layer 2 is formed by spraying or otherwise coating the patterned substrate with an liquid suspension of nanotubes, as is described in detail herein and in the incorporated references. For example, SWNTs or MWNTs may be conveniently dispersed in aqueous suspension at a desired concentration, particularly where functionalization treatment of the SWNTs assist in making the nanotubes hydrophilic. Alternative organic solvents may likewise be used to disperse and apply the nanotube film 2. See for example, U.S. patent application Ser. No. 10/846,072 entitled "Flexible Nanotube Transistors"; and L. Hu et al., Percolation in Transparent and Conducting Carbon Nanotube Networks, Nano Letters (2004), 4, 12, 2513-17, each of which application and publication is incorporated herein by reference.

In the example of FIG. 8A, the electrodes 3a, 3b are shown deposited upon substrate 9 beneath the SWNT film 2, as this advantageously permits the use of substrates having pre-printed or pre-patterned electrode material, which permits substantial costs savings in volume production. However, other electrode configurations are possible without departing from the spirit of the invention.

Figure 8B:
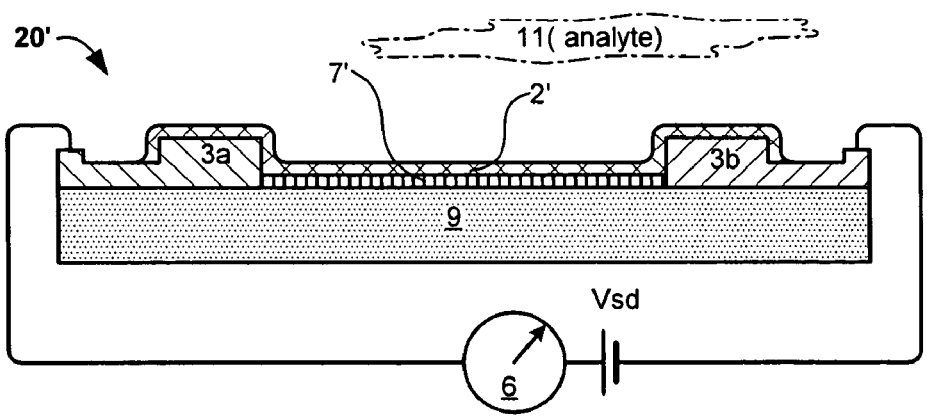

In the example shown in FIG. 8A, an optional functionalization or recognition layer 7 is included in association with the layer 2. This applied following deposition of SWNT film 2. In the example shown in FIG. 8B, a layer of recognition material 7' is deposited upon the substrate prior to application of the nanotube film 2, and is disposed underneath film 2. In either of the examples of FIGS. 8A and 8B, a recognition material may penetrate the nanotube network 2 so as to be incorporated as a mixture.

FIG. 8A shows an optional additional passivation, protective or inhibiting layer 8 may cover electrodes 3 and all or a portion of layers 2 and 7.

Figure 8C:
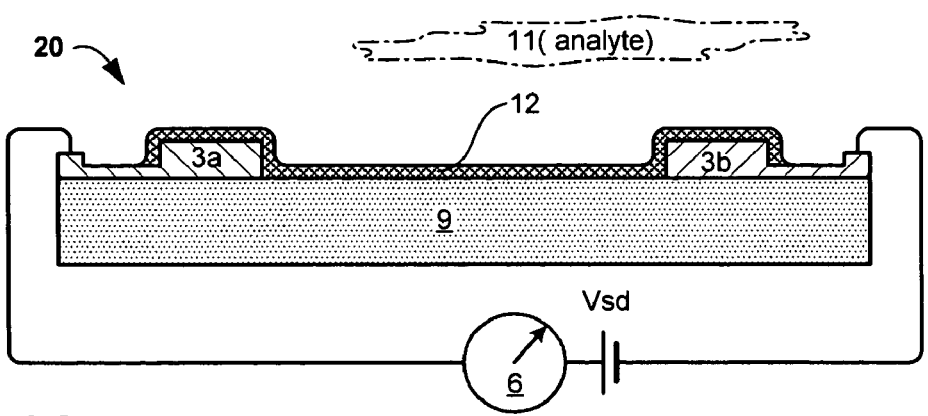

In certain embodiments, recognition or detection material is deposited, reacted or bound to the nanotubes (or alternative nanostructures) prior to deposition of layer 2. Depending on the selected detection chemistry and analyte target, such pre-functionalization may eliminate the need for any distinct recognition layer 7. In the example shown in FIG. 8C, a layer of pre-functionalized nanotubes 12 is deposited upon the substrate, without any separate application of a recognition or functionalization material.

The nanostructure layer 2 may be deposited stepwise, with intermediate drying, to permit the density and conductivity of the layer 2 to be accurately controlled, such as by probe-testing the layer resistance or conductance between deposition steps, until a selected layer conductivity or resistance is achieved.

Suitable measurement circuitry is included in communication with electrodes 3a and 3b (and any optional additional electrodes), here represented by meter 6 and source-drain power source Vsd.

D. Exemplary Sensor Having a Pre-Functionalized Nanotube Network

Figure 9:
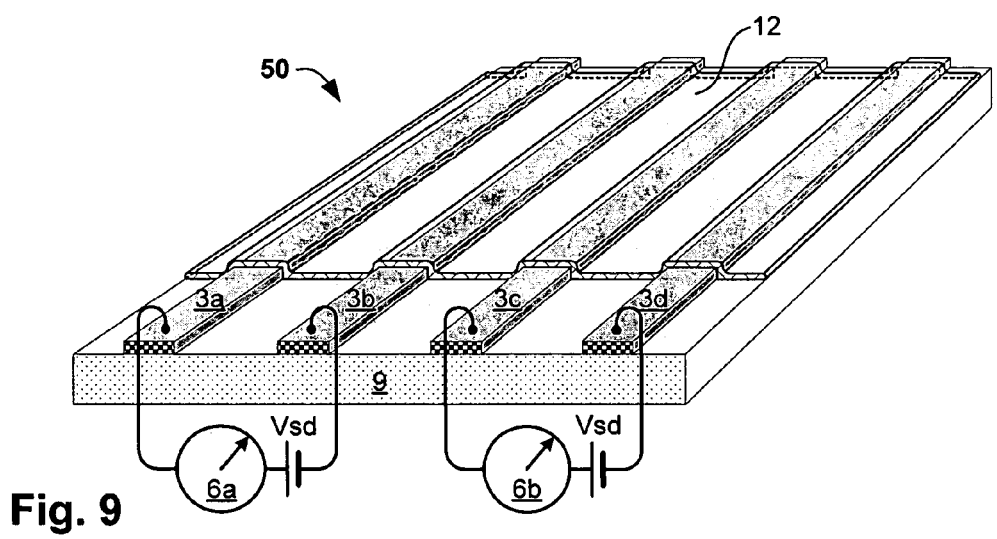
FIG. 9 shows an exemplary embodiment of a sensor device 50 having aspects of the invention and including a nanotube networks fabricated by deposition of a solution of pre-functionalized nanotubes upon a substrate.

Sensor fabrication. FIG. 9 shows an exemplary embodiment of a sensor device 50 having aspects of the invention and including a nanotube networks fabricated by deposition of a solution or dispersion of nanotubes upon a substrate 9 to form a nanotube film 12. In an exemplary embodiment shown in FIG. 9, the nanotubes (or other nanostructures) are dispersed in a volatile solvent which evaporates following deposition to leave the nanotubes configured as an open network 12.

Although electrical contacts may be deposited or applied subsequent to nanotube deposition, it is convenient and advantageous to pattern desired electrode or contact material 3 upon the substrate 9 prior to nanotube deposition (four contacts 3a-3d are shown). For example, substrates (e.g., polymer sheets such as PET, polystyrene, polycarbonate and the like) are commercially made having printable conductor material applied in a selected pattern (e.g., carbon, silver, gold, silver/silver chloride, mixtures and the like). A suitable flexible PET substrates with a pattern of printed conductive carbon traces may purchased from Conductive Technologies, Inc., of York, Pa., for example, a flexible PET substrate with screen-printed carbon paste electrodes, with spacing between the conductive traces of about 1 mm. A plurality of devices may conveniently be fabricated on a sheet of substrate material, and may subsequently be partitioned and packaged as desired, either as single sensor devices, or as arrays of sensors, and the like.

In an exemplary embodiment having aspects of the invention, the nanotube network was formed from SWNTs which were functionalized by covalently bonded poly-(m-aminobenzene sulfonic acid ("PABS"). Carbon nanotubes, preferably SWNTs, may be reacted and treated with PABS (composite referred to as "SWNT-PABS") by the methods as described in B Zhao et al, "Synthesis and Properties of a Water-Soluble Single-Walled Carbon Nanotube-Poly(m-aminobenzene sulfonic acid) Graft Copolymer", Adv Funct Mater (2004) Vol 14, No 1 pp 71-76, which article is incorporated by reference. A suitable nanotube composite material ("SWNT-PABS") may be obtained from Carbon Solutions, Inc. of Riverside, Calif. in the form of a dry powder.

A variety of alternative functionalization species may be included, such as conductive polymeric materials, polyaniline (PANI), polypyrrole, polyaniline derivatives, and the alternative materials described above in TABLE 3. See, for example, the electrochemical treatments described in T Zhang et al, "Nanonose: Electrochemically Functionalized Single-Walled Carbon Nanotube Gas Sensor Array", Proc. 208th Meeting of Electrochemical Society (Los Angeles, Calif. Oct. 16-21, 2005), which is incorporated by reference.

A suitable aqueous deposition solution may be made by suspending SWNT-PABS powder in water (preferably at a concentration of about 1 mg/mL), and ultrasonication may be employed to assist in making a homogeneous dispersion. The carbon nanotube dispersion may be sprayed with an air brush to coat the substrate.

Preferably the deposition is done in several light coating steps with intermediate drying (for example on a hotplate with the temperature of about 55 to 75 degree C.). The film resistance may be measured between steps until the selected resistance is obtained (the measurement may be between printed traces, or may be by pin probes on the network coating. For example, the deposition may be continued until resistance with a half-inch pin probe spacing is about 15 K Ohm.

Figure 10:
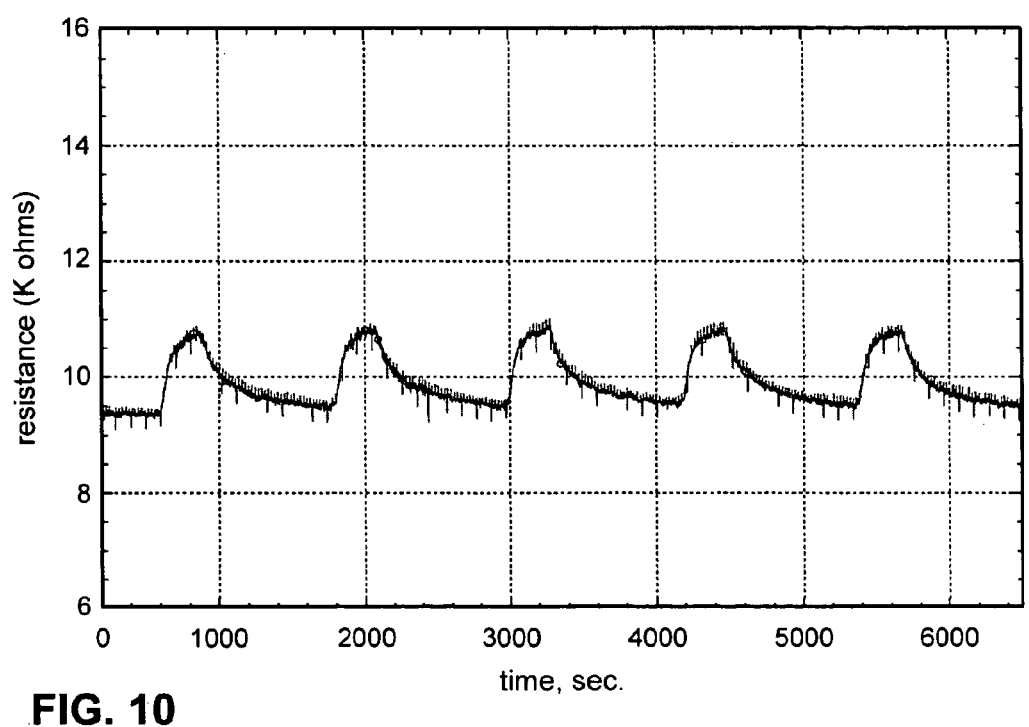
FIG. 10 shows the response of the sensor of FIG. 8 to repeated exposures of 50 ppm of ammonia.
Figure 11:
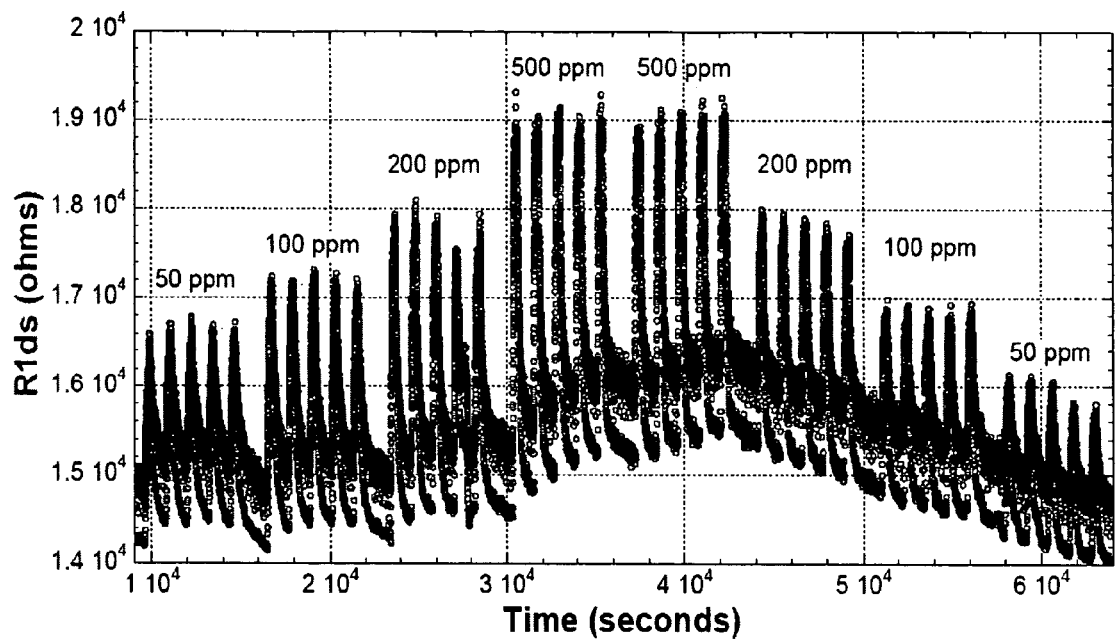
FIG. 11 shows the response of the sensor of FIG. 8 to ammonia exposures through a dynamic range spanning 50 ppm to 500 ppm.

Ammonia Detection. FIGS. 10 and 11 are plots showing the response of the sensor described above with respect to FIG. 8 to ammonia in an automated gas test station. The selected ammonia concentrations were obtained by dilution with nitrogen in a computerized gas dilution system. Prior to measurements, the sensors were purged with nitrogen for 30 min followed by exposure to ammonia for 15 min. The ammonia gas was switched to nitrogen for 5 min between successive test experiments.

FIG. 10 shows the response of the sensor to repeated exposures and recovery at 50 ppm of ammonia. The response may be seen to be repeatable and consistent.

FIG. 11 shows the response of the sensor to repeated exposures and intermediate recoveries throughout a 10 fold dynamic range, beginning at 50 ppm, grading upwards to 500 ppm, and grading downward back to 50 ppm. The response may be seen to be generally repeatable and consistent throughout this range. The exemplary sensors rapidly recover their resistance when NH3 is replaced with argon.

The forgoing embodiments provide advanced chemical sensors based on chemically functionalized single-walled carbon nanotubes (SWNTs). The inclusion of conductive or semiconductive polymeric functionalization material may improve sensor performance for detection of NH3 (e.g., covalently attached poly-(m-aminobenzene sulfonic acid forming a SWNT-PABS composite). The exemplary sensors have ppm sensitive, rapid response, and rapidly recover when NH3 exposure ceases.

E. Exemplary Environmental Control and Actuator System

Figure 12:
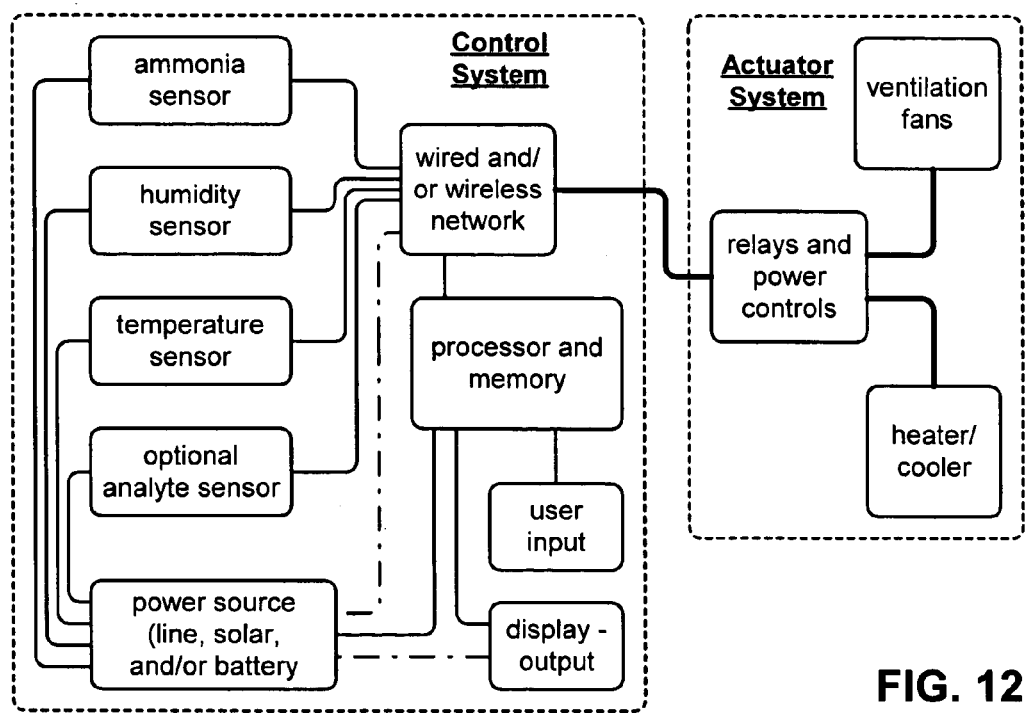
FIG. 12 is a schematic layout diagram of an exemplary environmental control system including a nanoelectronic ammonia sensor having aspects of the invention.

FIG. 12 is a schematic layout diagram of an exemplary environmental control and actuator system including a nanoelectronic ammonia sensor having aspects of the invention. Preferably a plurality of sensing modalities are employed to optimize environmental conditions in an enclosure, such as a poultry house, by controlling ventilation, heating and optionally air cooling. In the example shown, the control system includes at least one ammonia sensor, and optionally a humidity sensor, a temperature sensor, and a sensor specific to an additional environmental gas, contaminant vapor or other species, such as CO2, NOx, O3, CH4, H2S, CO, allergens, pathogens, or the like.

The sensors may be powered by any convenient method, such as line power, batteries, solar cells, and the like. The sensors communicate with a computer processor or microprocessor which includes memory. The processor is preferably is in communication with a user input and output/display device, such as a monitor and keyboard. Either wired or wireless communication (or a combination of these) may be employed, for example including conventional network hardware, to connect sensors the processor. Alternative the system may be integrated into a single control module.

For example, it may be advantageous to have a particular sensor (e.g., ammonia) mounted in a wireless remote module, such as is described in U.S. patent application Ser. No. 11/111,121 filed Apr. 20, 2005 (publication 2006-0055,392) entitled "Remotely communicating, battery-powered nanostructure sensor devices"; which is incorporated by reference. The described nanosensors having aspects of the invention have very low power dissipation, and therefore lend themselves to compact remote installations powered, for example, by a small battery and/or photovoltaic cell. The described remotely communicating sensor devices can be interrogated as needed by a processor located at another convenient location.

Remote sensor modules permit monitoring an environmental variable at a plurality of locations, and determining ventilation or other control response based on a composition of sensor outputs. Additionally, reliability and accuracy may be improved by including redundant sensors for a particular environmental variable, such as humidity or ammonia, and analyzing sensor outputs to determine a most reliable value for the variable based on statistical or quality control algorithms. See for example the methods described in the above referenced U.S. Pat. No. 5,407,129 issued to Carey et al.

The processor, memory and user I/O devices permit a user to set control points, review measurement histories, track quality control variables, and/or determine sensor status or maintenance histories, and the like. The processor may also be configured to monitor heater and ventilator fan performance. Conventional feedback control algorithms may be employed to optimize environmental control.

An environmental actuator system communicates with and responds to commands of the control system, so as to maintain ammonia, humidity and temperature (and optionally an additional analyte) within programmed limits. The actuator system includes such devices as ventilation fans, heaters, and optionally air coolers. The actuator system may also include scrubbers, filters, particle removers and the like to condition air quality. Generally, ventilation and heater units dissipate power at a higher order of magnitude than the control system sensor and processor functions, and the actuators may conveniently be operated by relays and other conventional power controls, in response to processor commands.

One of ordinary skill in the art may combine elements of FIG. 12 in alternative ways without departing from the spirit of the invention. For example, it may be advantageous in industrial applications of the control system of FIG. 12 to integrate the control system with a particular actuator modality as a modular control-actuator system. This may be done to simplify installation and maintenance, and to facilitate the economical retrofitting of poultry houses as existing ventilation and heating equipment reaches its service life. Thus, a ventilation unit may be supplied with an integrated environmental control system, and a separate heater unit may be supplied with a separate integrated environmental control system.

F. Alternative Sensor Configurations

It should be understood that the embodiment shown in FIG. 8 is exemplary, and a number of alternative configurations are possible without departing from the spirit of the invention. Some examples are shown in FIGS. 13A-13E, including alternative embodiments of sensors having aspects of the invention and including nanotube networks fabricated by deposition of a solution upon flexible substrates with pre-patterned conductor traces. It should be understood that the vertical dimension is generally highly exaggerated for clarity, and that thin sheets of substrates, such a PET, may be printed or coated to very small tolerances with conventional conducting materials. Where the embodiments include generally similar elements, these are numbered the same.

Figure 13A:
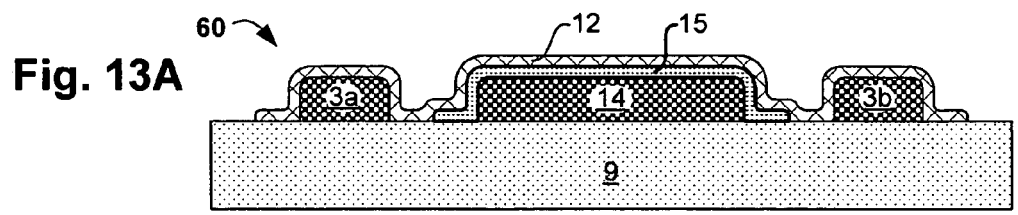

FIG. 13A shows a NTFET alternative sensor 60 having space-apart source and drain traces 3a and 3b disposed on substrate 9. An additional intermediate trace 14 is coated with a thin layer of dielectric material 15 (organic film or inorganic deposit) prior to deposition of nanotube layer 12, so as to form a gate electrode.

Figure 13B:
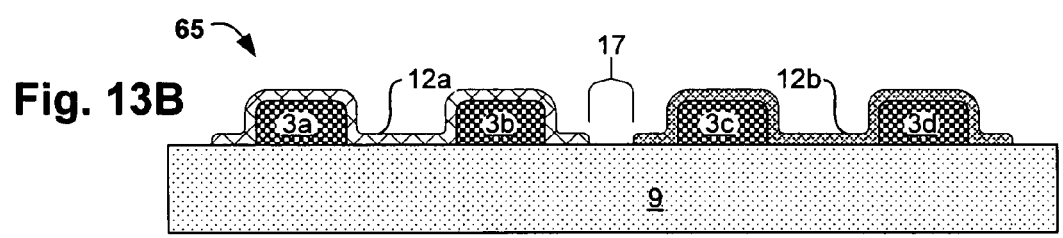

FIG. 13B shows a sensor 65, generally similar in configuration to that of FIGS. 8-9, and including a plurality of distinct pairs of space-apart patterned source and drain traces on a single substrate are coated with differently functionalized nanotube networks (e.g., traces 3a, 3b coated with nanotube layer 12a, and traces 3c, 3d coated with nanotube layer 12b), so as to have different sensing properties. A gap 17 between nanotube layer portions may be provided (by masking, scoring, and the like) so as to provide electrical isolation between nanotube layers 12a and 12b. Note that this configuration may also be employed to provide reference sensors or calibration sensors in an array format.

Figure 13C:
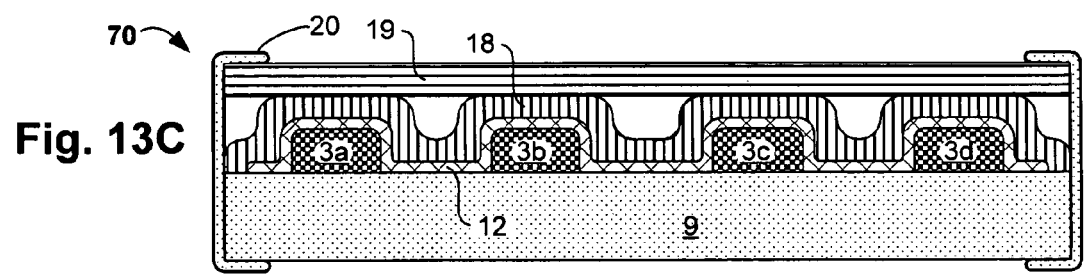

FIG. 13C shows a sensor 70 generally similar to that shown in FIGS. 8-9, and having additional layers of encapsulation or covering material which functions to filter or condition the ambient medium so as to improve selectivity or to protect the sensor. In this example, nanotube layer 12 is covered by either or both of an encapsulation layer 18, and a filter lamination layer (fixed, e.g. by adhesive or taped edges 20). These additional layers 18, 19 can provide a low-cost integrated sensor unit which is protected by the layers (e.g., hydrophobic coatings permeable to the analyte of interest) and with reduced cross-sensitivity (filters selectively absorbing a cross-contaminant, such as NOx). Such layers 18, 19 may cover all or only a portion of the sensor surface, for example, to isolate a reference sensor from the environment while leaving a measurement sensor exposed. The 18, 19 may also provide abrasion resistance to protect delicate nanotube films, to permit convenient user handling, such as in a disposable sensor.

Figure 13D:
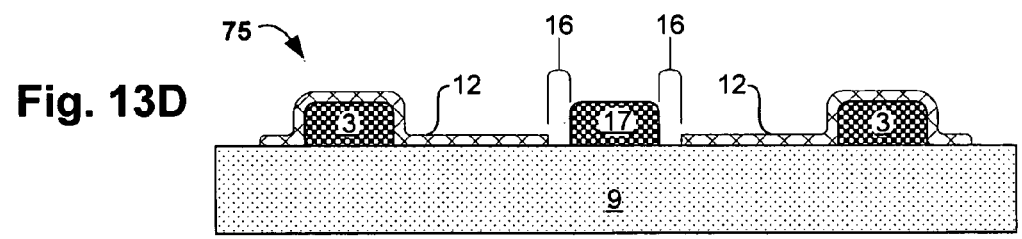

FIG. 13D shows a sensor 75 configured as a capacitance sensor in which a nanotube network 12 connects to at least one trace 3, and is separated from at least one other counter-electrode trace 17 by a defined gap 16 (e.g., gap made by masking, scoring, or the like). Conventional circuitry may be used to measure the change in capacitance of the nanotube layer 12 with respect to the counter electrode 17 in response to an analyte.

Figure 13E:
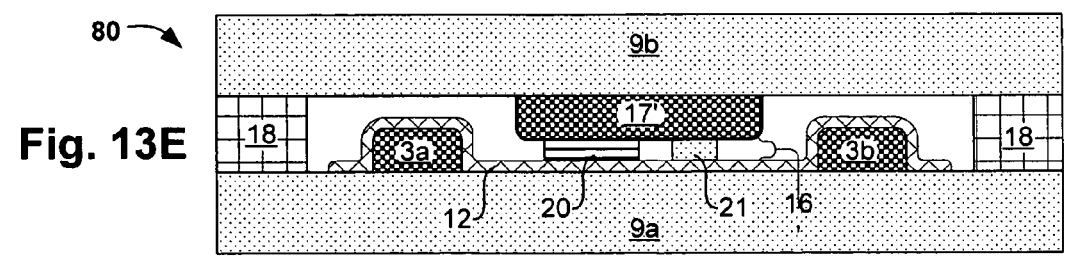

FIG. 13E shows alternative embodiment 80 of a capacitance sensor in which a second substrate 9b having a counter-electrode trace 17' is laminated to a first substrate 9a having a nanotube network 12, the counter electrode being maintained in a spaced apart arrangement from the nanotube network by spacers to maintain gap 16'. The spacers may include edge spacers 18 which do not contact the nanotube layer 12 in the region of gap 16'. Alternatively or additional, the device may include a thin porous sandwich spacer 20 which provides a dielectric separation between electrode 17' and layer 12 while permitting the diffusion of analyte. Alternatively, a non-porous dielectric intermediate spacer 21 may be interposed between a portion of counter electrode 17' and layer 12 to control the dimension of gap 16', while leaving other portions of electrode 17' and layer 12 exposed to analyte.

It should be noted that spacer-controlled lamination of substrates similar to that shown in FIG. 13E may be included in sensor embodiments such as those of FIG. 13A-13D, so as to create an enclosed lumen or volume for analyte medium, suitable for microfluidic sensors and the like.

FIGS. 14A-14E illustrate an exemplary embodiment of a sensor system having aspects of the invention, including a disposable sensor generally similar to the embodiment of FIGS. 8-9, and including a sensor mounting socket suitable for integration into an instrumentation module, such as an environmental control system.

It should be noted that while sensors generally similar to that shown in FIGS. 8-9 may have a long service life, the low cost, low power properties of the sensor embodiments having aspects of the invention lend themselves elf to a disposable or easily replaceable sensor module. In many applications, it may be advantageous to replace a low-cost sensor at regular intervals, (simplifying calibration and quality control procedures. In addition, a "generic" sensor socket may be configured to accept sensors for different analytes or different concentration ranges, making the control module conveniently re-configurable or upgradable.

Figure 14A:
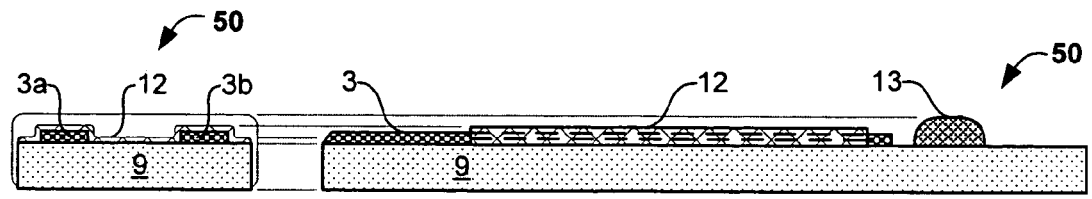

FIG. 14A shows, in cross section and longitudinal section view, an exemplary embodiment of a disposable sensor device 50 having aspects of the invention and including a nanotube network 12 arranged on substrate 9. Nanotube network 12 connects with one or more conductive traces or contacts 3 disposed on substrate 9. As may be seen in the left-hand cross section view of FIG. 14A, in this example the contacts 3 include a spaced-apart source-drain pair of traces 3a and 3b. The layer 12 is functionalized for sensitivity to an analyte of interest, for example ammonia. As may be seen in the right-hand longitudinal section view of FIG. 14A, in this example the contacts 3a and 3b extend beyond the network layer 12 to be exposed adjacent the end of substrate 9. A sealant portion 13 (e.g., an elastomer material) is disposed on substrate 9 at the end opposite the exposed contacts.

Figure 14B:
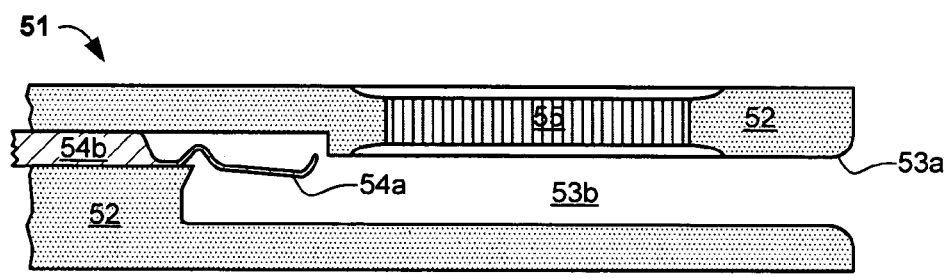

FIG. 14B shows in longitudinal section view an exemplary embodiment of a sensor mounting socket 51 having aspects of the invention and suited to mounting the sensor 50 of FIG. 13A. The socket 51 includes a body 52 having a central slot 53b terminating at one end in opening 53a. At the opposite end of slot 53a, the body 52 mounts one or more conductive pins 54b which have a spring contact portion 54a protruding into slot 53b. On one side of body 52 is mounted a sensor orifice/filter 55.

Figure 14C:
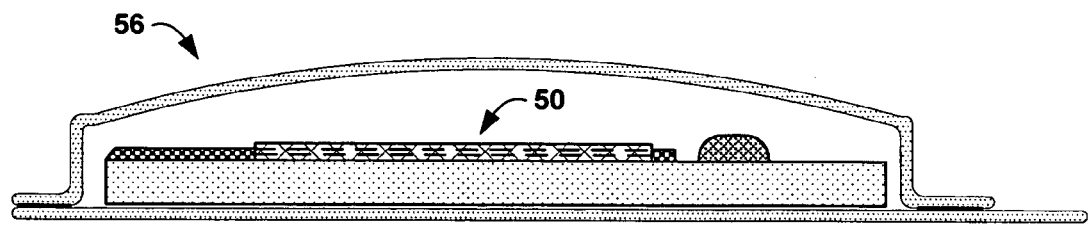

FIG. 14C shows, in longitudinal section view, the disposable sensor 50 of FIG. 14A as sealed in a conventional "blister pack" type protective package 56 having a peelable backing. The package 56 may be hermetically sealed, pre-sterilized, and/or protects the sensor 50, for example from abrasion, humidity and contamination, while providing the sensor ready for immediate use.

Figure 14D:
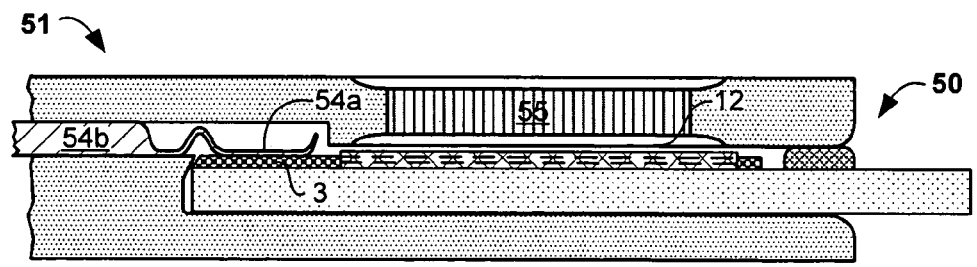

FIG. 14D shows the disposable sensor 50 of FIG. 14A as mounted in the sensor mounting socket 51 of FIG. 14B. Note in this example (although not shown in side section), pins 54 include an electrically isolated parallel pair of pins 54b and spring contacts 54a corresponding and communicating with traces 3a and 3b respectively of sensor 50. Note also that nanotube layer 12 of the mounted sensor 50 lies adjacent orifice/filter 55, which is permeable to at least the analyte of interest. The sealant portion 13 contacts the opening 53a of slot 53b, so as to seal the opening when the sensor is mounted. The sensor 50 in this example may be held firmly in place by friction applied by one or both of sealant 13 and spring contacts 54a (additional or alternative closures and the like may be included).

Figure 15:
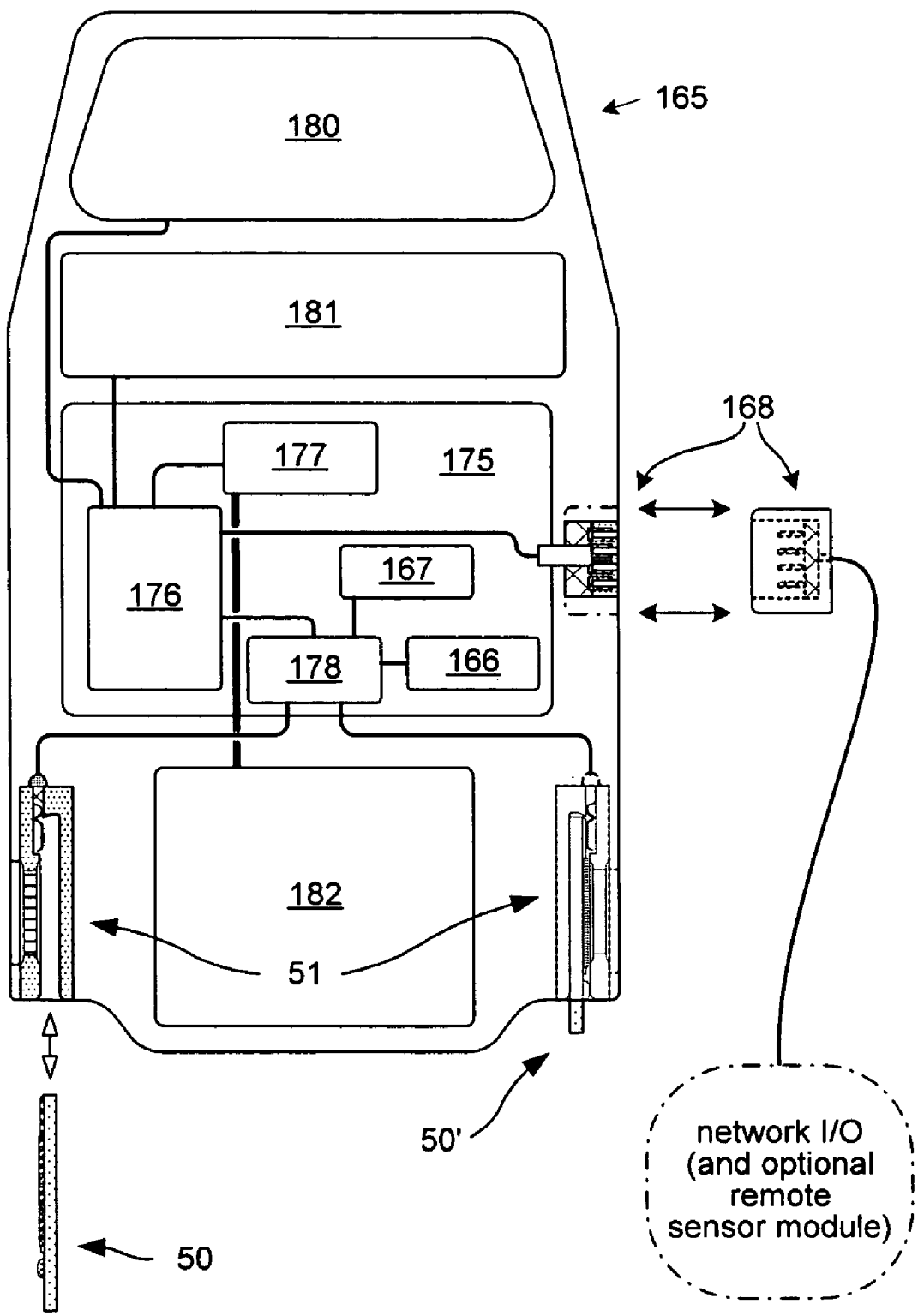
FIG. 15 shows an exemplary embodiment of a control system employing the disposable sensor and socket of FIGS. 14A-14D.
Figure 16:
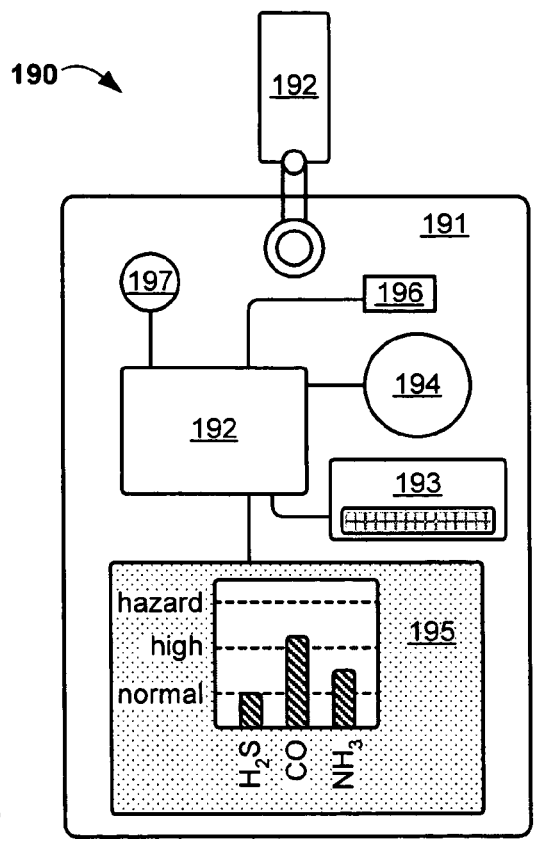
FIG. 16 shows an exemplary embodiment of a personnel safety badge having aspects of the invention.

FIG. 15 shows an exemplary embodiment of a control system unit 165 employing a sensor having aspects of the invention, such as the disposable sensor 50 and socket 51 of FIGS. 14A-14E. The unit 165 may include many or all of the functional elements shown in the control system of FIG. 12, packaged in a convenient product configuration, such as a battery-powered wall-mounted unit accepting disposable analyte sensors. In this example, unit 165 includes a circuit board 175 for mounting power supply 177, A/D converter 178, microprocessor/memory module 176, wireless or wired I/O connections 168, thermistor 166, RH sensor 167, and the like. The processor board is shown connected to one or more sensor sockets 51 mounting disposable sensors 50 and 50'. The unit 165 also includes a display 180 and a keypad 181.

G. Sensor Arrays, and Low Cost Safety Badge Example

Optionally, The various embodiments of nanoelectronic sensors describe in the above examples may comprise a plurality of sensors disposed in a pattern or array, 0.15 such as described in prior application Ser. No. 10/388,701, entitled "Modification Of Selectivity For Sensing For Nanostructure Device Arrays" (now U.S. Pat. No. 6,905,655), which is incorporated by reference herein. A sensor array embodiment may provide for a number of advantageous measurement alternatives, methods and benefits according to the invention, for example:

a. multiple analytes detected by a plurality of specifically functionalized sensors,
b. improve the signal/noise ratio or increase the robustness of the device.
c. increased precision and dynamic range by a plurality of sensors each of which is optimized for a different range,
d. increased analyte specificity and flexibility by detecting a characteristic "profile" of responses of a target analyte to a plurality of differently-functionalized sensors,
e. self calibration systems and isolated reference sensors,
f. multiple-use array having a plurality of deployable one-time-use sensor sub-units, or
g. ultra-low-cost, direct-digital-output sensor arrays, including a plurality of sensors, each producing a binary signal, and collectively having a range of response thresholds covering a selected analyte concentration range.

Low cost substrate sensors having aspects of the invention generally similar to the embodiments shown in FIGS. 8-9 and FIGS. 13A-13E are well suited to applications such as industrial safety badges and similar equipment.

FIG. 15 shows an exemplary embodiment of an industrial personnel safety badge 190 having aspects of the invention, comprising a card mount or badge body 191 supported by a swivel clip 192 suitable for attaching the card 190 to a pocket, shirt lapel, jacket or article of clothing (a cord or necklace may also be employed). The badge 190 may includes compact, low-cost electronic components generally similar to those found in inexpensive electronic watches, musical gift cards, and the like. Badge 190 is shown including a battery 194, an integrated microprocessor 192 and an user-readable display such as LCD 195. At least one sensor, and preferably a multi-analyte sensor array (see FIG. 12B) having aspects of the invention is mounted to the card 191, arranged so as to sample air next to the card surface, and is connected to processor 192. The display 195 in this example is simple a bar graph showing levels of one or more toxic analytes, such as $NH_3$, $CO$, and $H_2S$, organic vapors and the like.

Additionally or alternatively to display 195, badge 190 may include sound alerts such as beeper 196 to alert to hazardous analyte levels. Light alerts such as flashing LED 197 may be pre-programmed to alert to hazardous levels also. In additional alternatives, badge 190 may include active or passive RFID-type elements or other wireless communication components (not shown) to provide for remote monitoring of personnel exposure to toxic analytes. The processor may also include memory configured to maintain analyte-specific exposure history, downloadable to permanent record computers.

H. Suspended Network Sensor

Figure 17:
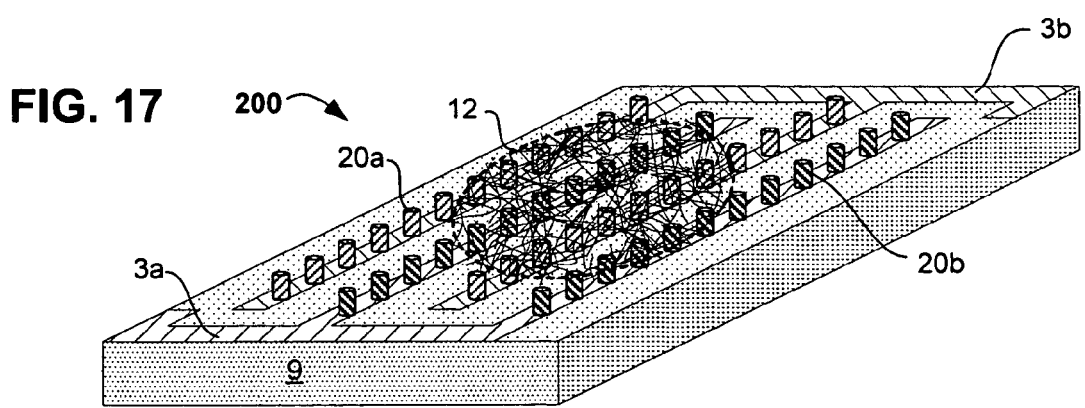
FIG. 17 shows an exemplary embodiment of a sensor having a network suspended apart from a substrate.

FIG. 17 shows an additional exemplary embodiment of a sensor device 200 having aspects of the invention and including a nanotube network 12 arranged so as to be suspended above and spaced apart from substrate 9. In this example, each of contacts 3a and 3b support a plurality of pillar-like conductors 20a and 20b respectively. Network 12 is supported by, and electrically communicates with, the pillars 20a, 20b. The network 12 may be deposited by a number of methods described herein, such as by CVD growth (e.g., catalyst on pillars), by solution deposition, or by network transfer (e.g., from a vacuum deposited network on a porous substrate, rafted or transferred to adhere to the pillars). This embodiment permits the network 12 and any recognition material associated with it, to interact with analyte species isolated from substrate influence. Alternative embodiments are possible (such as a capacitive sensor) without departing from the spirit of the invention.

I. Method of Dynamic Sensor Sampling

In one inventive aspect, a method of dynamic sensor sampling is provided, which permits measurement of analyte concentration over time, while avoiding exposure of the sensor to a sample medium on a continuous basis. For example, a valve or fluidic circulation system may be included to selectively expose a sensor having aspects of the invention to a sample medium. In certain embodiments, a dynamic sampling method permits minimizing exposure of a sensor to corrosive or life-limiting environmental conditions. In other embodiments (e.g., and electrochemical sensor), a dynamic sampling method may conserve reagent supply and extend service life. In yet other embodiments, a dynamic sampling method may avoid irreversible or persistent changes in sensor properties. In still other embodiments a dynamic sampling method may permit more rapid sensor response to changes in analyte conditions and reduce recovery time. A dynamic sampling method may also be employed to reduce cross-sensitivity, where response to a cross-reactant is slower than to a target analyte.

Figure 18:
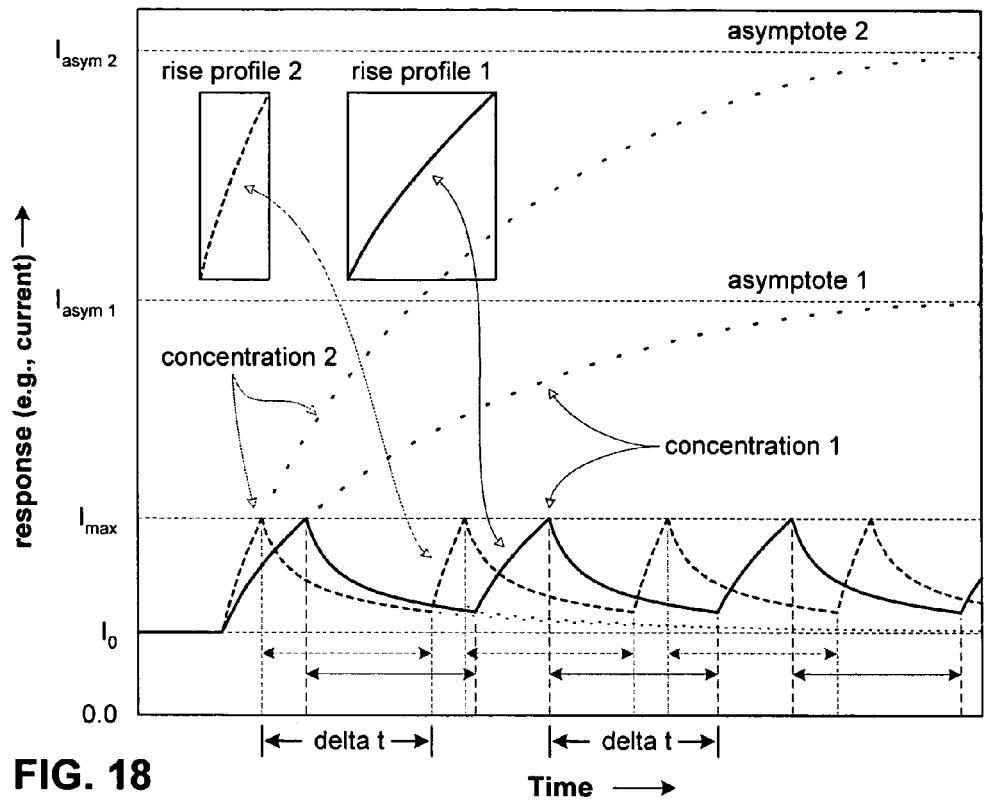
FIG. 18 is a schematic plot illustrating principles of a dynamic sensor sampling method having aspects of the invention.

FIG. 18 is a schematic plot illustrating principles of a dynamic sensor sampling method having aspects of the invention. The vertical axis represents a nominal sensor response magnitude. In the example shown, this is an electrical current/(e.g., across a channel element of a transconductance sensor) but the response may represent any one of a number different sensor properties, such as a conductance, resistance, capacitance, impedance or the like. The response may also represent a complex or derived property, such as a ratio, modulation, time constant, exponent or other relationship associated with measured properties. The response may alternatively represent a statistical property in relation to multiple sensors of a sensor array, such as a mean value or the like.

As may be seen in FIG. 18, the unexposed sensor is initially at an response level ($l_0$). Exposure of the sensor to a first analyte concentration (concentration 1) produces a sensor response that increases over time so as to asymptotically approach (dotted curve) a steady-state response magnitude ($l_{asym1}$). If the sensor is isolated from exposure to a sample (or otherwise prevented from responding to an analyte, such as by a controllable inhibitor) at a point when the response reaches a selected cut-off magnitude ($l_{max}$), a recovery trend is begun, the response value declining so as to asymptotically approach the intial value $l_0$. If the sensor is again exposed to the analyte sample after a recovery interval (delta t), the sensor response again increases ("rise profile") in a similar manner until the cut-off value $l_{max}$ is reached.

A second curve in FIG. 18 represents the response of the sensor to an analyte sample of a differing concentration (heavy dashed line-concentration 2), such that the response that increases over time so as to asymptotically approach (dotted curve) a different steady-state response magnitude ($l_{asym2}$). If the exposure is interrupted at a cut-off value ($l_{max}$), and the sensor is permitted to recover for a selected interval (delta t), the response curve of concentration 2 is similar to that of concentration 1, but having a differing rise profile (rise profile 1 vs. rise profile 2). Analytical comparison of the rise profiles may be employed to characterized the analyte concentrations, without monitoring the sensor response until a steady-state response magnitude is reached or approached.

Figure 19:
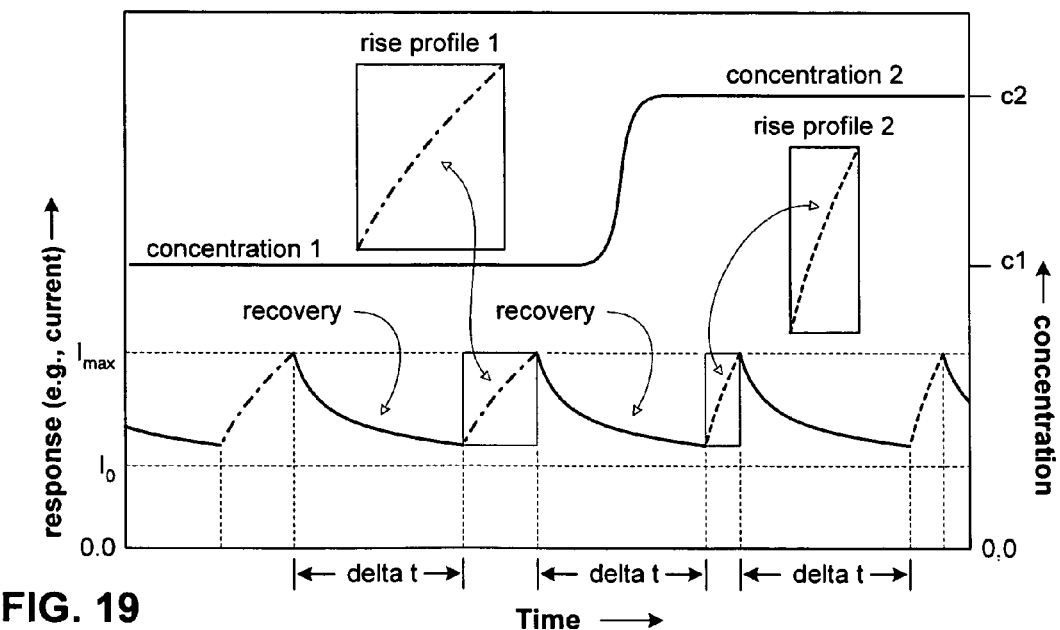
FIG. 19 is a schematic plot an example of dynamic sensor sampling for a step change in analyte concentration, having a fixed response cut-off values and recovery interval.

FIG. 19 is a schematic plot an example of dynamic sensor sampling for a step change in analyte concentration. As in FIG. 18, the sampling method in this example applies a fixed maximum response cut-off value $l_{max}$ and a fixed recovery interval delta t. The curve of sensor response shows a change in rise profile following the change in analyte concentration (rise profile 1 vs. rise profile 2). It should be understood that in the example shown, the sensor recovery is consistent, independent of analyte concentration, and approaches ($l_0$) without a persistent off-set. However, this may not be so, and methods of dynamic sampling may be applied effectively to sensors which do not exhibit these characteristics. For example, accumulated drift in sensor response may be compensated for. A number of alternative analytical algorithms may be applied to correlate rise profile with analyte concentration.

Figure 20:
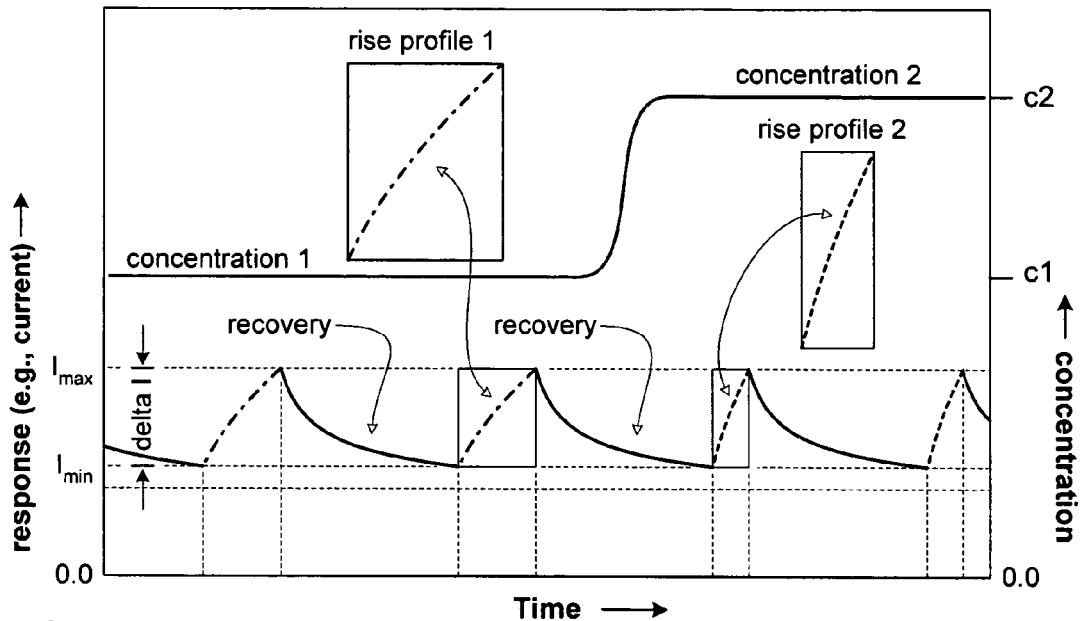
FIG. 20 is a schematic plot an example of dynamic sensor sampling for a step change in analyte concentration, having both fixed maximum and minimum values.

FIG. 20 is a schematic plot an alternative example of dynamic sensor sampling for a step change in analyte concentration, having both fixed maximum and minimum response cut-off values. As may be seen, the measurement and recovery phases (analyte exposure and isolation) are triggered by a response magnitude reached a maximum and minimum value ($l_{max}$ and $l_{min}$).

Figure 21:
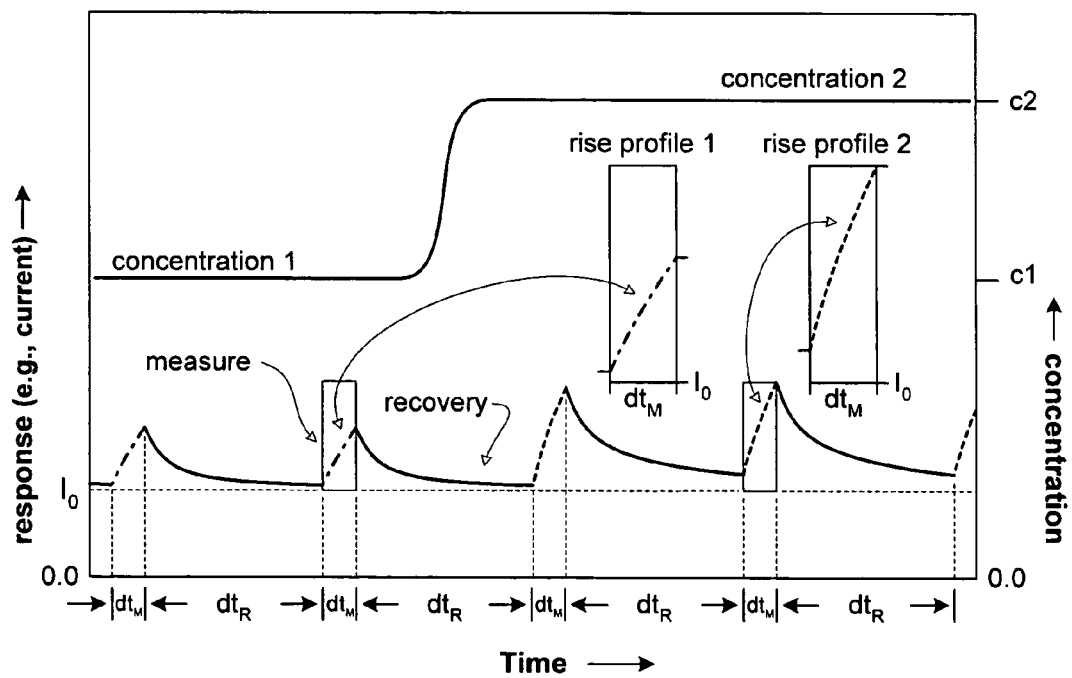
FIG. 21 is a schematic plot an example of dynamic sensor sampling for a step change in analyte concentration, having a both fixed measurement and recovery intervals.

FIG. 21 is a schematic plot an example of dynamic sensor sampling for a step change in analyte concentration, having a both fixed measurement and recovery intervals. As may be seen, the measurement and recovery phases are triggered by the passage of a determined measurement interval ($dt_M$) and recovery interval ($dt_R$).

It should be understood that a sensor system may employ the sampling modes of FIGS. 18-21 alone, in sequence or in combination. For example, a sensor system may be programmed to apply a certain sampling mode for analyte concentrations in a certain range and another sampling mode for another range of analyte concentrations for a stand-by or active mode, or the like. Additional alternative modes of sampling may be employed without departing from the spirit of the invention.

In like fashion to that described in the example above, alternative functionalization materials and alternative device architectures may be included (e.g., alternative electrode elements and nanostructures, such as nanowires, MWNTs, non-carbon or hetero nanotubes other known nanoparticles, and the like). Such alternatives may include measurements of other device properties, such as capacitance, impedance and the like.

Figure 22:
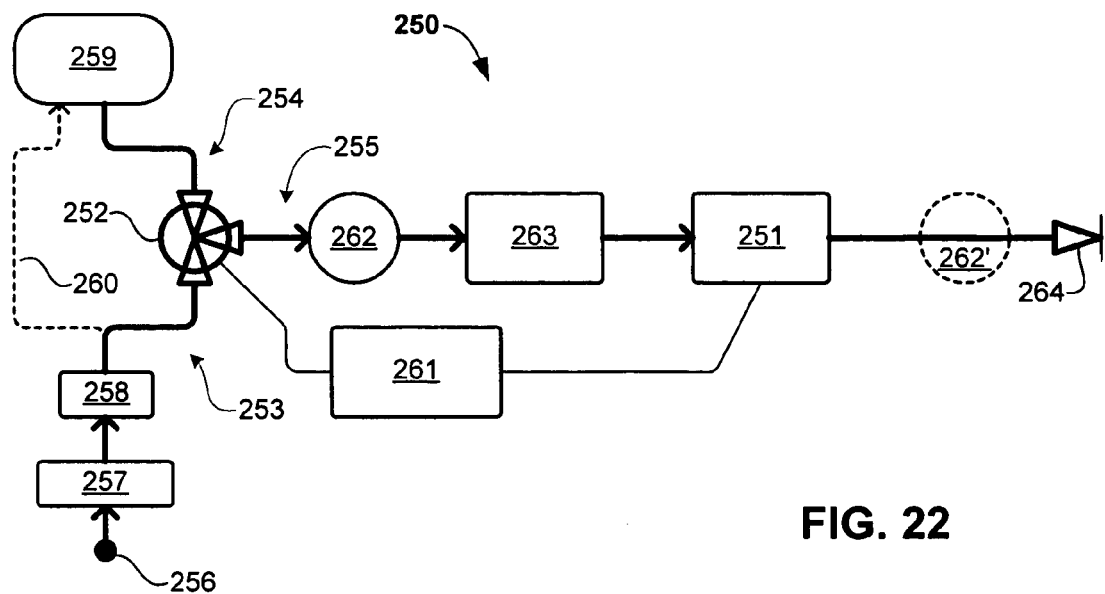
FIG. 22 is a schematic diagram of an exemplary sensor system configured for employing a dynamic sampling method.

FIG. 22 is a schematic diagram of an exemplary embodiment of a sensor system 250 having aspects of the invention, and configured for employing a dynamic sampling method. System 250 includes a controllable selector valve 252 which interconnects to a sampling fluid path 253, to a purge fluid path 254, and to a measurement fluid path 255.

System 250 comprises a sensor 251 disposed on measurement fluid path 255, which may include one or more of any of the nanoelectronic sensor embodiments described herein. Sensor 251 may alternatively or additionally comprise any one of a number of alternative sensor types, such as electrochemical sensors, SAW sensors, optical sensors, CMOS sensors and the like.

In an example system 250 for the monitoring and/or control of an ambient environment, such as ammonia ($NH_3$) content of the air within a poultry house, sampling path 253 may comprise an inlet 256 from an environmental space which preferably connects to a filter 257 configured to remove particulates from the sample air. Additional treatment or filter component 258 may be included to remove interferents or contaminants, for example $H_2S$, from the sample, or may additionally or alternatively include a de-humidifier, such as a cold-trap.

Purge path 254 may comprise purge gas source 259, such as a source of purified air, dry $N_2$, and the like. In one example, purge source 259 comprises sample air having additional filtering or treatment to remove the analyte of interest (e.g., $NH_3$ absorbent), fed in this example from the sampling path 253 by bypass 260.

Measurement path 255 receives a multiplexed flow provided by selector valve 252 sequentially comprising sample air and purge air. In this example the selector valve is controlled by processor 261 which is in communication with sensor 251, and may be configured for sampling/purge (measurement/recovery) sequences such as are illustrated in FIGS. 18-21. Alternatively, the multiplexing sequence may be controlled by other mechanisms, such as fixed timers and the like.

The multiplexing sequence may be selected to apply a duty cycle for sensor measurement, such as on the order of a few percent or less. For certain types of sensor with finite measurement life due to factors such as reagent exhaustion (e.g., many electrochemical sensors), a fractional duty cycle can extend effective sensor life by orders of magnitude.

Air flow is induced by pump 262 which connects to optional temperature controller 263 (heater and/or cooler), which in turn supplies multiplexed flow (at a selected temperature) to expose sensor 251. Following sensor exposure, the multiplexed flow is emitted at exhaust 264.

It should be understood that a number of alternative arrangements of system 250 are possible without departing from spirit of the invention, and that the system may be configured for measurement of a broad range of different analytes in different sample mediums (i.e., dissolved analytes in aqueous media). For example, the pump may be provided downstream (262') from sensor 251, and/or may be provided upstream of selector valve 252 (not illustrated). In certain measurement applications the pump may be omitted, as where sample and/or purge flow is provided by other means (e.g., natural convection, fans for space ventilation, gravity flow, pressurized environmental spaces, and the like).

Figure 23:
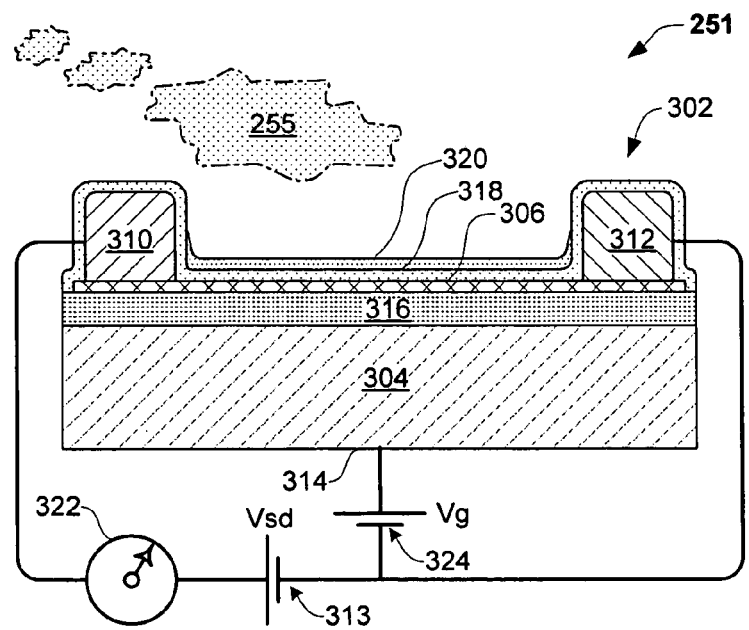
FIG. 23 illustrates the structure of a sensor adapted for measuring NH3, for example in a system such as is shown in FIG. 22.

FIG. 23 illustrates the structure of an exemplary sensing device 251 having aspects of the invention and adapted for measuring an analyte, such as $NH_3$, contained in measurement medium 255, for example in a system such as is shown in FIG. 22. The architecture of sensor 251 is generally similar to that shown in FIG. 1. Sensing device 251 includes a nanostructure sensor 302 configured as a field effect transistor, comprising a substrate 304 having a dielectric surface layer 316. Substrate 304 may be comprise a conductive material, such as doped silicon, permitting it to function as a gate electrode. A spaced-apart pair of contacts 310, 312 (e.g., Ti/Au layers) are disposed in communication with SWNT channel 306. Circuitry 322 preferably includes controllable voltage sources 313 and 324 to regulate Vsd between contacts 31-312 and Vg applied at 314 to control the voltage of the substrate/back gate. As in the case of the sensor of FIG. 1, a number of alternative configurations are possible without departing from the spirit of the invention.

In the example shown, SWNT channel 306 is covered or passivated with thin a dielectric coating 318 which may comprise $Al_2O_3$, ZrO2 or the like, either alone, in mixtures, or in a multilayer coating. Coating 318 is preferably deposited by ALD and may be only a few nanometer in thickness (e.g., between about 10 and about 100 nm). A functionalization layer 320 is deposited above coating 318, and may comprise one or more of the materials listed in Table 3 above. In a preferred example, layer 320 may comprise glycerol, alone or in combination with a surfactant such as Triton 100.

A number of different measurement schemes may be advantageously applied in ammonia detection using sensor device 251. For example, temperature and humidity dependence of the device may be reduced by heating sample 255 to a temperature above the ambient (e.g. between about 60 and about 70° C.).

In one exemplary measurement protocol, the substrate gate or "back gate" 304 is grounded and a DC bias-voltage Vsd is applied between the source 310 and drain 312, so as to generate a measurable current through channel 306, permitting the determine of conductance or resistance as a function of exposure to medium 255 and/or as a function of time.

In an alternative measurement protocol, the Vg of the backgate 304 is modulated with a voltage waveform produced by circuitry 322. This waveform may have a particular shape (e.g., sin wave, triangle wave, square wave, etc), a particular amplitude (e.g., 1 mV peak-to-peak, 1 V peak-to-peak, 10 V peak-to peak, etc), a particular offset (e.g., −1 V, 0V, +1 V, etc), and/or a particular frequency (e.g., 0.1 Hz, 1 Hz, 10 Hz, etc). The conductance or other properties may then be measured at one point, or at multiple points during the gate-waveform. This protocol may produce measurements with increased stablility.

In an additional alternative measurement protocol, the AC gate voltage is applied to gate 304 as described above, and in addition a waveform AC-bias Vsd is applied between the source 310 and drain 312, and measurements of conductance or other properties is likewise taken at selected points within the Vsd waveform.

The employment of AC waveforms for Vg and/or Vsd can permit much faster response and recovery of sensor response. Such measurement protocols may stabilize the device and also reduce such effects as charge migration, electrochemical reactions, or other phenomena. Such AC measurement protocols can permit other parameters to be measured simultaneously (e.g., RH, temperature, and the like) which can then used in compensation algorithms to improve measurements of analyte concentrations In addition, global changes of the conductance response to Vg ("I/Vg") may be tracked. For example, 1) electron transfer shifts the I/Vg left or right along the gate-voltage axis, 2) charge-carrier scattering scales the I/Vg in the "conducting" region, 3) changes at any ohmic contact shifts the I/Vg up or down along the conductance axis. There are likely to be many more global changes than those listed here. A number of analog, digital, and/or software algorithms may be used to track such global changes. This information may be employed to increase the accuracy and precision of measurements, among other things.

Having thus described a preferred embodiment of nanostructures with electrodeposited nanoparticles, and methods of making them, it should be apparent to those skilled in the art that certain advantages of the within system have been achieved. It should also be appreciated that various modifications, adaptations, and alternative embodiments thereof may be made within the scope and spirit of the present invention. For example, specific examples have been illustrated for nanotube film nanostructures, but it should be apparent that the inventive concepts described above would be equally applicable to other types of nanostructures. The invention is further defined by the following claims.

The invention claimed is:

1. A method for controlling the operation of a sensor in monitoring an analyte in a sample environment, comprising:
   (a) selectively exposing at least a portion of a sensor to the environment so that the sensor portion is exposed only intermittently; and
   (b) dynamically sampling a response signal output from the sensor to determine the presence or concentration of the analyte by analysis of the dynamically sampled signal.

2. The method of claim 1, wherein selectively exposing includes regulating sensor exposure by means of one or both of a fluidic lumen and a valve.

3. The method of claim 1, wherein dynamically sampling includes analysis of the sensor signal limited to one or more of selected ranges of sensor response and selected time intervals of sensor exposure to the environment.

4. The method of claim 3, wherein dynamically sampling includes limiting the analysis of the response signal to response magnitudes below a cut-off maximum.

5. The method of claim 3, wherein selectively exposing includes regulating sensor exposure to provide for non-exposed recovery time periods.

6. The method of claim 5, wherein the non-exposed recovery time periods are of a selected fixed duration.

7. The method of claim 1,
   (a) wherein the sample environment includes at least one species which has a property effective to reduce the recovery time of the sensor, and
   (b) wherein the intermittent exposure of the sensor to the environment defines periods of exposure and periods of non-exposure, which periods of non-exposure are effective to reduce the recovery time of the sensor.

8. The method of claim 7 further comprising disposing a sensor apparatus including the sensor within the sample environment to monitor the concentration of the analyte within the sample environment.

9. The method of claim 7 further comprising monitoring the concentration of the analyte within a sample environment over a period greater than 20 days.

10. The method of claim 1 wherein the sensor comprises one or more nanostructured elements.

11. The method of claim 10 wherein the sensor portion comprises the one or more nanostructured elements.

12. The method of claim 10 wherein the one or more nanostructured elements comprise one or more carbon nanotubes.

13. The method of claim 1 further comprising analyzing the dynamic response signal to characterize an analyte concentration.

14. The method of claim 13 wherein analyzing the dynamic response signal comprises using a rise profile of a response curve to characterize an analyte concentration.

15. The method of claim 1, wherein the sensor is a field effect transistor-based sensor, and wherein the sensor portion is a nanostructured element spanning two electrodes.

16. A method for controlling the operation of a sensor in monitoring an analyte in a sample environment, comprising:
   (a) biasing a sensor using a fractional duty cycle; and
   (b) dynamically sampling a response signal output from the sensor to determine the presence or concentration of the analyte by analysis of the dynamically sampled signal, wherein the dynamic sampling depends on the concentration of the analyte such that a specific sampling mode is applied in response to the presence of a predetermined concentration of analyte.

17. The method of claim 16 wherein the fractional duty cycle is selected to enhance the sensor use life.

18. The method of claim 16 wherein the sensor is a nanotube-based sensor.

19. The method of claim 16 wherein the sensor is a nanotube-based electrochemical sensor.

20. A method for controlling the operation of a sensor in monitoring an analyte in a sample environment, comprising:
   (a) applying a multiplex fluid flow sequence to the sensor during reagent exposure to generate a dynamic response signal output, wherein applying a multiplex fluid flow sequence comprises biasing a sensor electrode using a fractional duty cycle;
   (b) analyzing the dynamic response signal output from the sensor to determine the presence or concentration of the analyte.

21. The method of claim 20 wherein the sensor is an electrochemical sensor.

22. The method of claim 20 wherein the sensor electrode is exposed to reagent during operation of the sensor.

* * * * *

UNITED STATES PATENT AND TRADEMARK OFFICE
CERTIFICATE OF CORRECTION

PATENT NO. : 8,152,991 B2
APPLICATION NO. : 11/636360
DATED : April 10, 2012
INVENTOR(S) : Briman et al.

It is certified that error appears in the above-identified patent and that said Letters Patent is hereby corrected as shown below:

At Line (75) Inventors:

1. Change the inventor name "Shirpal C. Gandhi" to --Shripal C. Gandhi--.

Signed and Sealed this
Twenty-fourth Day of July, 2012

David J. Kappos
*Director of the United States Patent and Trademark Office*